United States Patent [19]

Freese et al.

[11] Patent Number: 4,648,264

[45] Date of Patent: Mar. 10, 1987

[54] MULTI-FUNCTION APPARATUS FOR TESTING A SAMPLE OF MATERIAL

[75] Inventors: Dwight L. Freese; Emory L. Frey; Randall B. Cogbill, all of Duncan, Okla.

[73] Assignee: Halliburton Company, Duncan, Okla.

[21] Appl. No.: 757,094

[22] Filed: Jul. 19, 1985

[51] Int. Cl.$^4$ ............................................. G01N 11/14
[52] U.S. Cl. ........................................... 73/64.1; 73/60
[58] Field of Search .................................. 73/64.1, 60

[56] References Cited

U.S. PATENT DOCUMENTS 4,299,118  11/1981  Gau et al. ................................. 73/60
4,484,468  11/1984  Gau et al. ................................. 73/60

OTHER PUBLICATIONS

SPE 9285 "Transition Time of Cement Slurries Between the Fluid and Set States".
"Description of Stirring Chamber"–5 pages.
Copy of p. 3897 taken from vol. 41 of the Halliburton Services Sales and Service Catalog.

Primary Examiner—Jerry W. Myracle
Assistant Examiner—Joseph W. Roskos
Attorney, Agent, or Firm—James R. Duzan; E. Harrison Gilbert, III

[57] ABSTRACT

A compact, transportable apparatus includes test equipment for operating on a sample of slurry within a single container to determine the compressibility, thickening time, and static gel strength of the sample. The static gel strength test is particularly performed with a load cell vertically moved along a lead screw, which load cell is directly connected to a drive mechanism for driving a paddle at a very slow speed through the sample.

20 Claims, 23 Drawing Figures

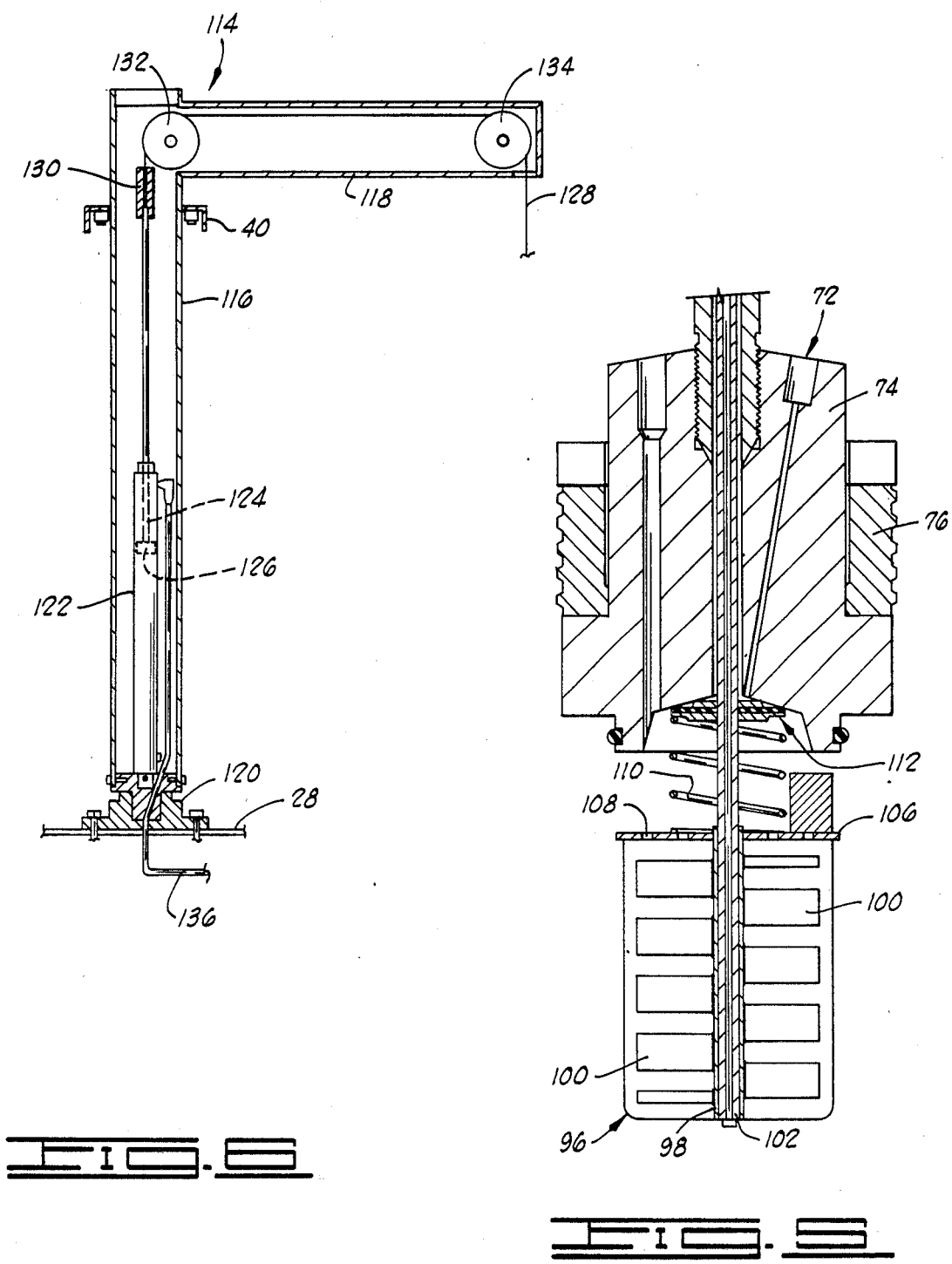

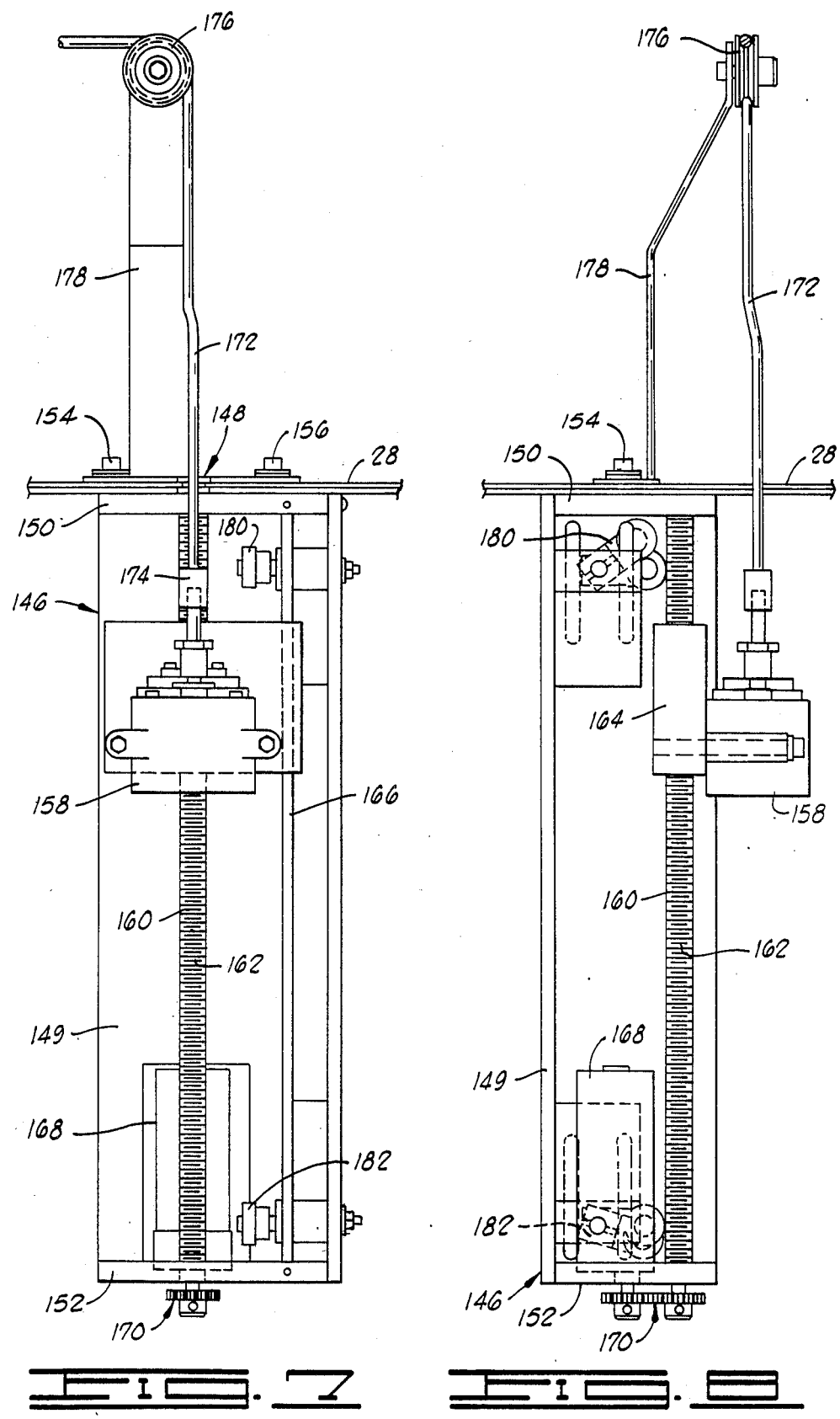

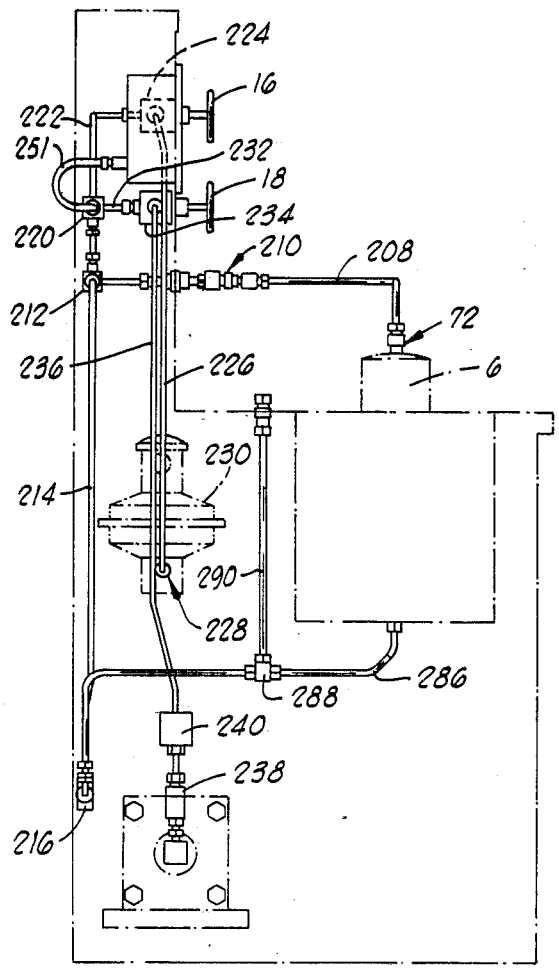
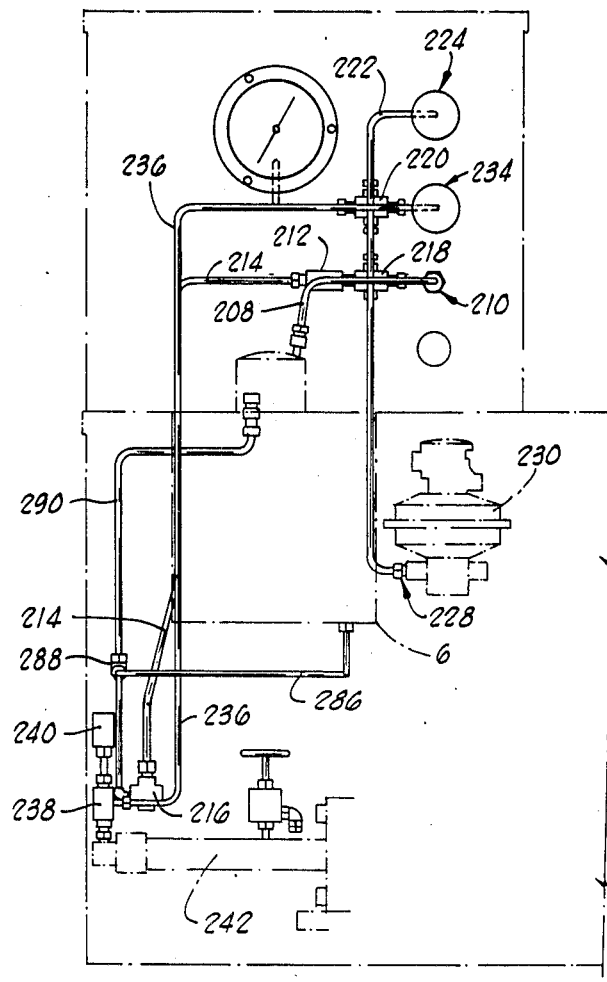

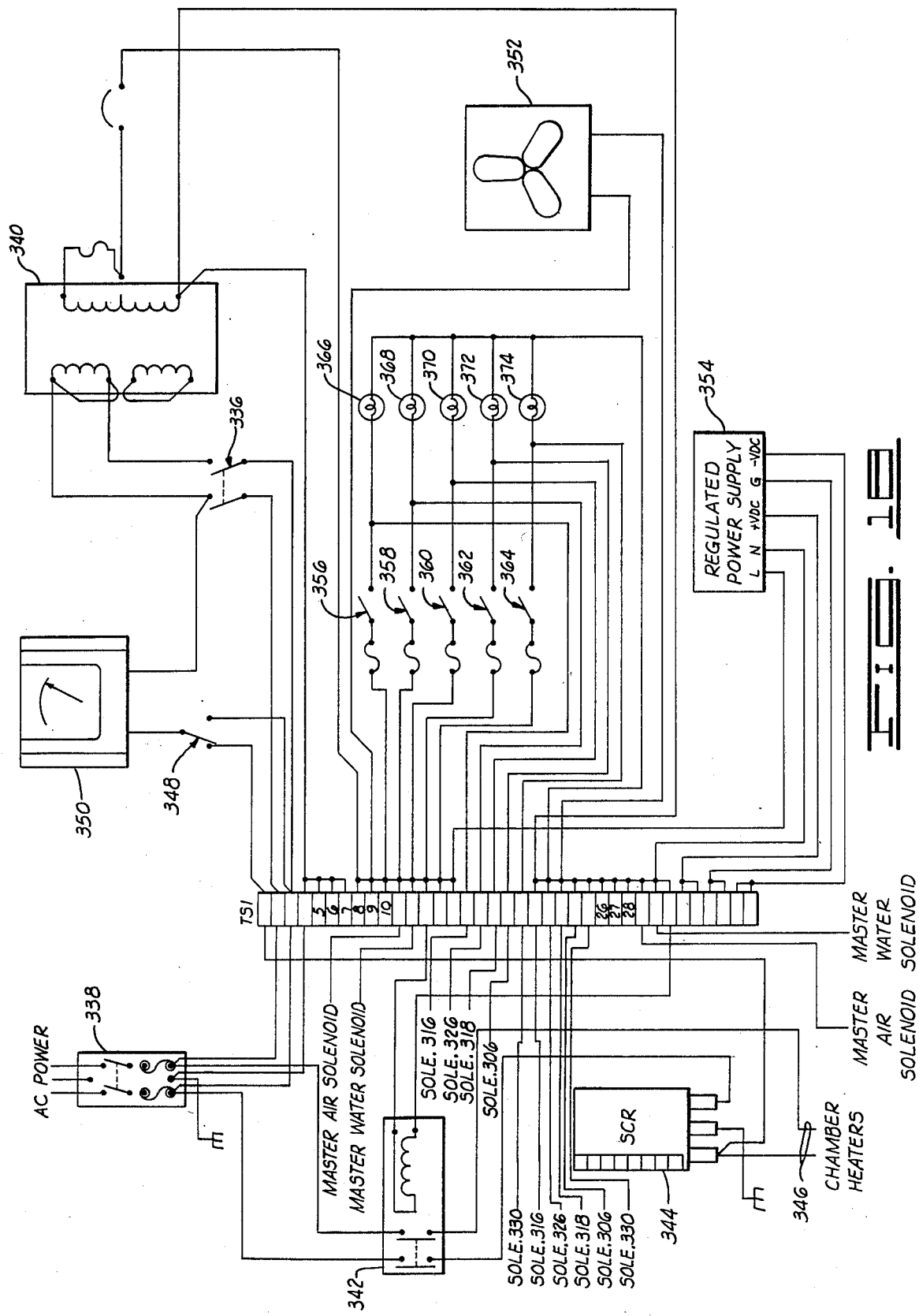

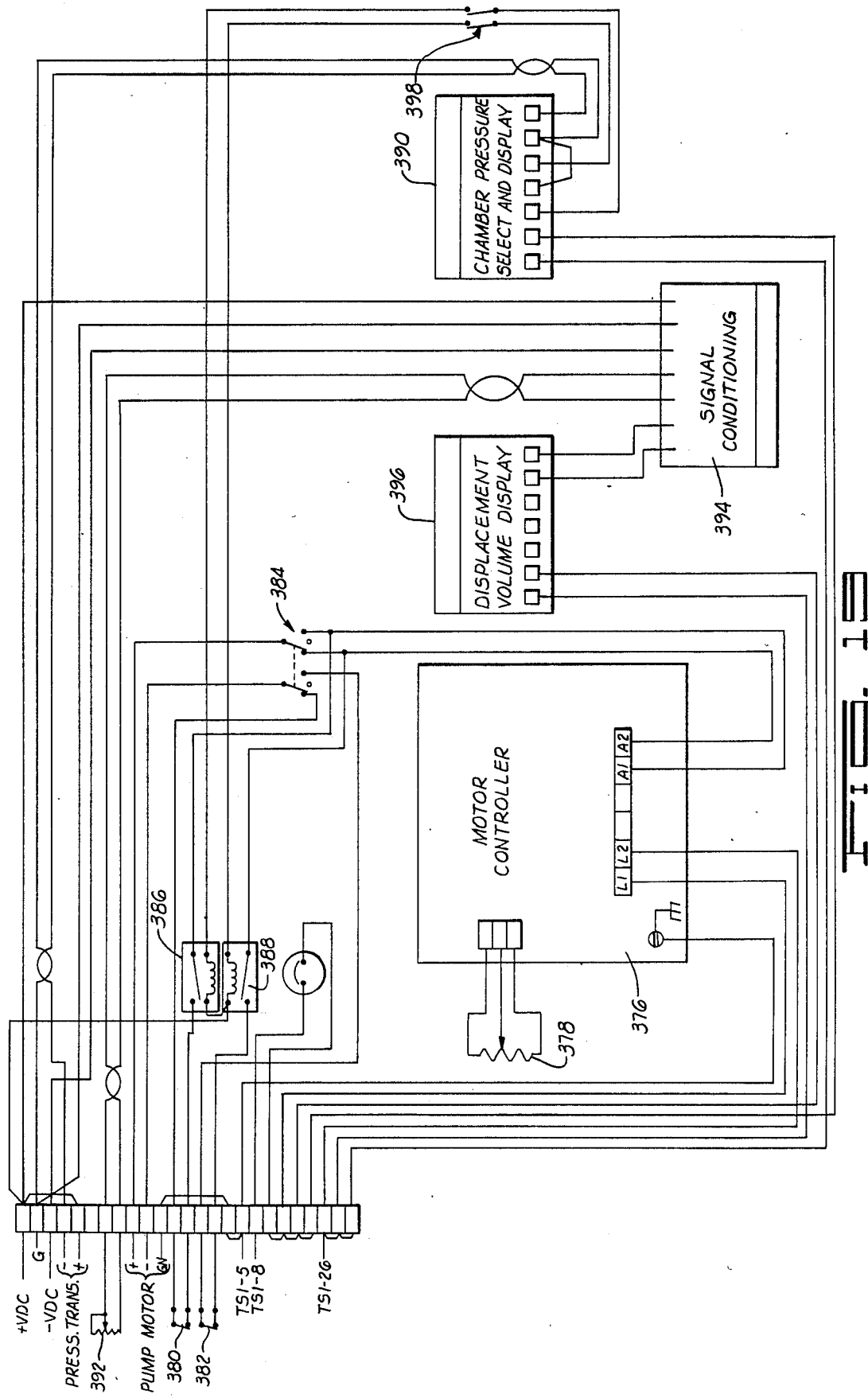

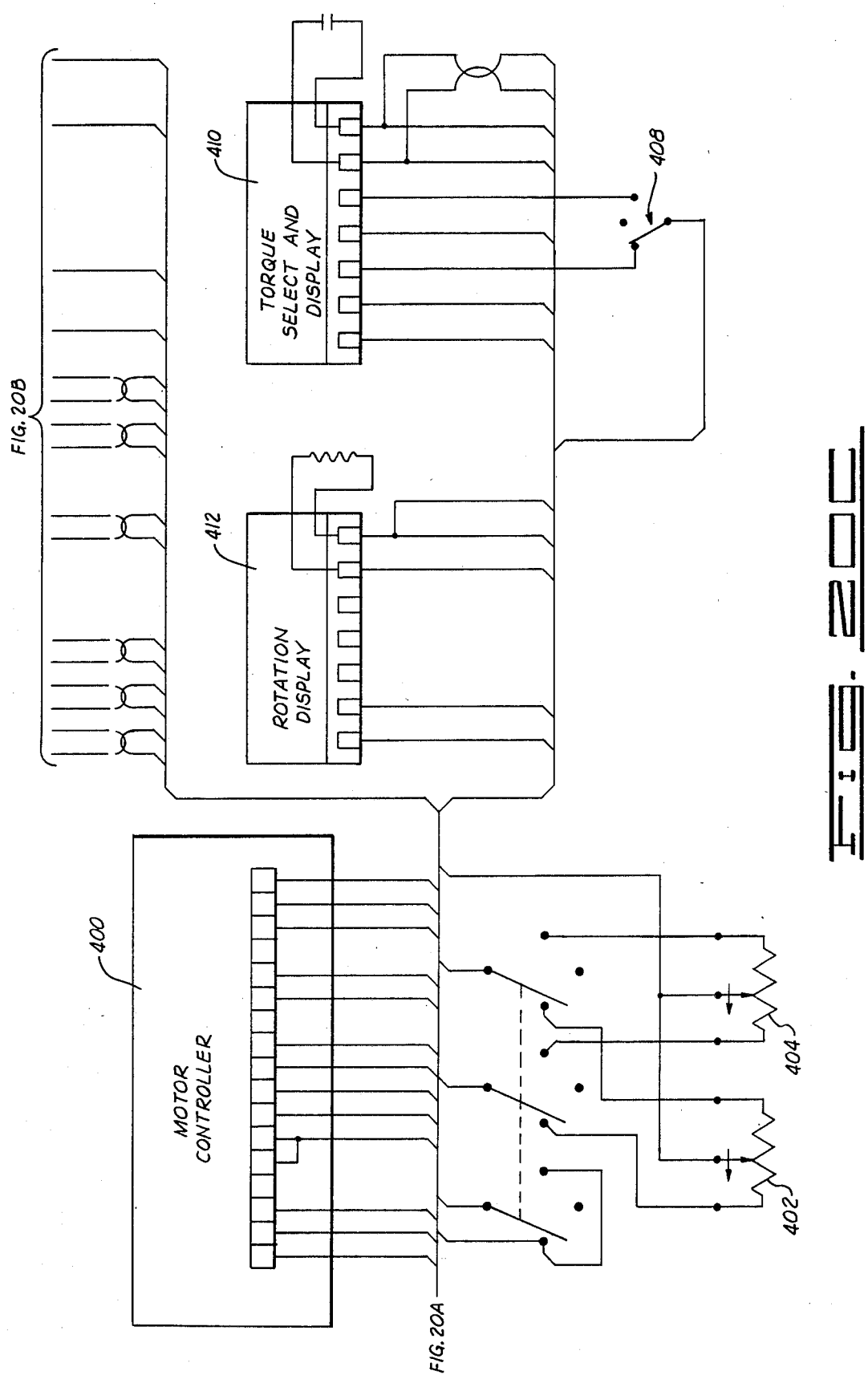

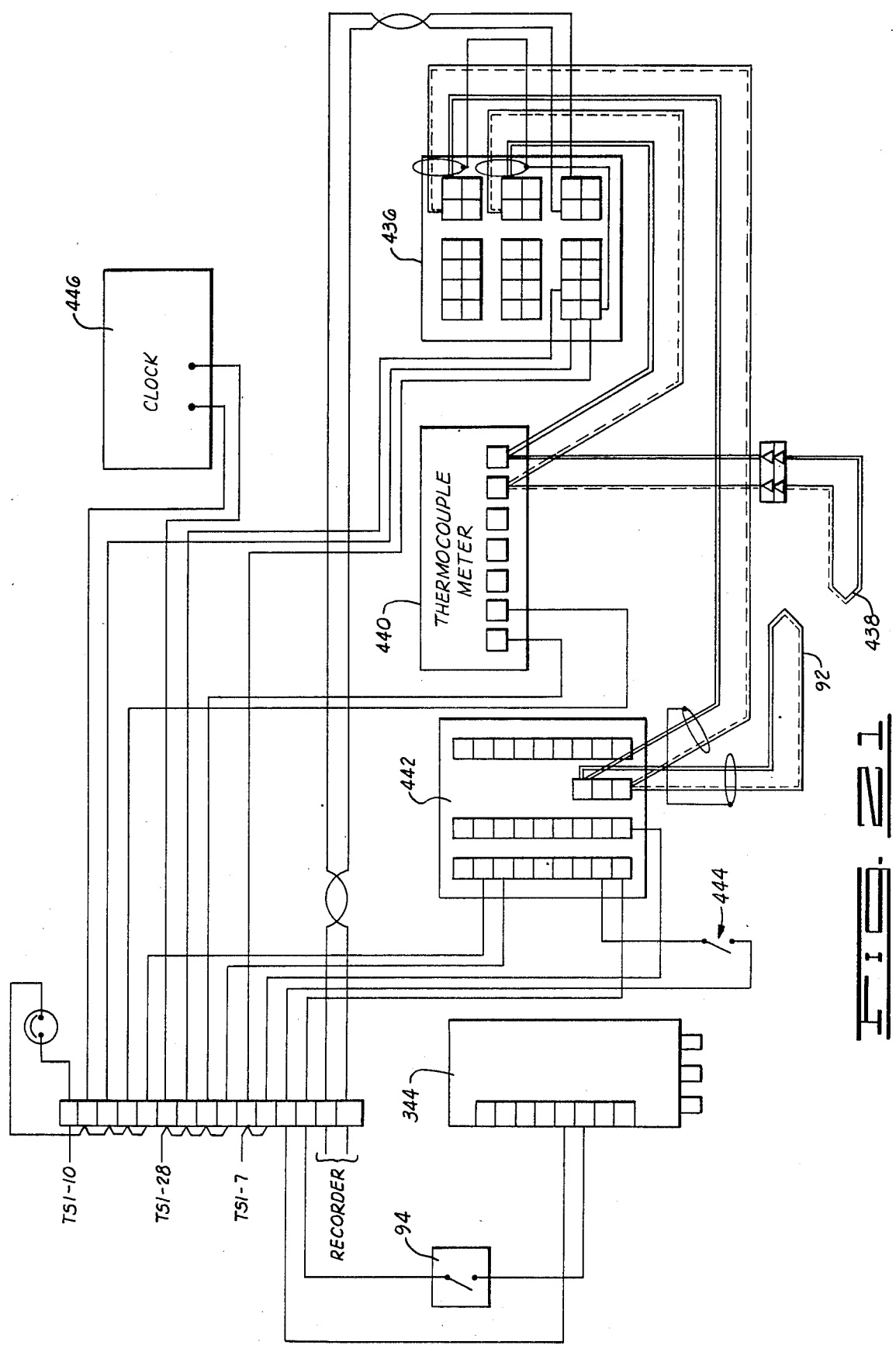

MULTI-FUNCTION APPARATUS FOR TESTING A SAMPLE OF MATERIAL

BACKGROUND OF THE INVENTION

This invention relates generally to apparatus for performing tests on fluids, such as cement to be pumped into a well, and more particularly, but not by way of limitation, to compact, transportable apparatus for performing static gel strength, thickening time and compressibility tests on a sample of cement.

In the oil and gas industry, different fluids are used for various purposes in drilling and completing a well. For example, batches of cement must be made and pumped into the well for cementing the casing into the well bore. The cement is generally pumped through the casing for flow back up the annulus between the well casing and the well bore to create the necessary bond.

Because different batches of fluids can have different characteristics which affect how the fluids perform in the high temperature and high pressure environments found downhole, there is the need for equipment which can perform different tests on a fluid sample prior to the fluid being pumped downhole so that one can determine if that particular batch of fluid has the proper characteristics for the particular situation. For example, three characteristics of fluid cement are known to be important. One is the static gel strength, or more specifically, the time it takes a static quantity of the cement to reach a predetermined gel strength. The static gel strength is important to know because it relates to the ability of the cement to prevent gas leaks when the cement is flowed into the annulus. If the cement will not properly gel, gas may create channels through the cement to the surface causing a hazardous situation. The static gel strength also relates to the ability of the cement to flow, which indicates how long the cement slurry can be pumped. Another important characteristic is the thickening time for the cement to reach a predetermined thickness or consistency. This characteristic also relates to how long the cement can be flowed before it begins to set up. Still another important characteristic to know is the compressibility of the cement. This characteristic is also pertinent to the gas leakage considerations for which the static gel strength test is performed. However, the compressibility test determines the hydrogen content resulting from additives in the cement slurry, which hydrogen content allows one to determine the shrinkage or swelling to be expected as the cement is flowed into the well and sets up. Because these characteristics vary with respect to different pressures and temperatures, there is the need for equipment with which these tests can be conducted under selectable pressures and temperatures simulating the environments in which the particular batch of fluid will be used.

The desirability of performing such tests on fluids, such as cement, has been known. Various types of equipment have also been built and used to perform one or more of these tests. For example, consistometers for measuring thickening time and viscometers for measuring viscosity have been used. We are aware that Halliburton Services has performed static gel strength, thickening time and compressibility tests on cement samples, in particular. However, we are not aware of a compact and transportable apparatus which performs these three specific functions with the components combined in the manner described and claimed herein.

SUMMARY OF THE INVENTION

The present invention provides a novel and improved apparatus for performing static gel strength, thickening time and compressibility tests on fluid samples at selectable pressures and temperatures. The present invention is compactly constructed and is transportable so that the invention can be readily used in relation to actual batches of fluid prepared in the field.

Broadly, the multi-function apparatus of the present invention comprises a cabinet; container means, having a chamber defined therein, for receiving the sample of material in the chamber, the container means connected to the cabinet; a paddle rotatably disposed within the chamber; first paddle drive means, connected to the cabinet, for rotating the paddle at a first speed so that the sample is maintained relatively static within the chamber despite the paddle rotating at the first speed; second paddle drive means, connected to the cabinet, for rotating the paddle at a second speed so that the sample is agitated within the chamber by the paddle rotating at the second speed; heater means, connected to the container means, for heating the sample within the chamber; pressurizing means, mounted on the cabinet, for applying a pressure to the sample within the chamber, the pressurizing means including pump means for extracting a measurable quantity of the sample from the chamber, the pump means having a plunger movably disposed therein; static gel strength test control means, mounted on the cabinet, for controlling the first paddle drive means, including: first speed control means for setting an angular speed at which the first paddle drive means rotates the paddle; first set point means for selecting a set point representative of a predetermined static gel strength; first sensor means for sensing an input force applied by the first paddle drive means to rotate the paddle in response to the first speed control means; and means, responsive to the first set point means and the first sensor means, for indicating when the sensed input force equals the set point representative of the predetermined static gel strength; thickening time test control means, mounted on the cabinet, for controlling the second paddle drive means, including: second speed control means for setting a rotational speed at which the second paddle drive means rotates the paddle; second set point means for selecting a set point representative of a predetermined consistency; second sensor means for sensing a parameter proportional to the torque applied by the second paddle drive means in response to the second speed control means; and means, responsive to the second set point means and the second sensor means, for indicating when the sensed parameter equals the set point representative of the predetermined consistency; compressibility test control means, mounted on the cabinet, for controlling the pump means, including: third speed control means for setting a speed at which the plunger of the pump means moves; directional control means for controlling the direction the plunger of the pump means moves; third sensor means for sensing a pressure of the measurable quantity of fluid extracted by the pump means; fourth sensor means for sensing a volume of the measurable quantity of fluid extracted by the pump means; and display means, responsive to the third and fourth sensor means, for displaying the sensed pressure and volume; and temperature control means, mounted on the cabinet, for controlling the heater means to heat the sample to a selectable temperature.

The temperature control means includes two sensors, one of which senses the temperature of the container means and the other of which senses the temperature of the sample received in the container means. The apparatus further comprises strip chart recorder means, mounted on the cabinet, for visually recording the temperatures sensed by the temperature sensor means and for visually recording a parameter in response to a selectable one of the sensor means associated with the static gel strength test control means and the thickening time test control means. The apparatus further comprises a fluid-actuated hoist means, connected to the cabinet, for raising and lowering the paddle relative to the container means.

Other features of the present invention broadly include a rupture disk and a pressure gauge which are connected in continuous communication with the chamber. The apparatus also includes a fluid system including two fluid inlet circuits, each having a master solenoid which is responsive to a master on/off switch mounted on the cabinet. The fluid system further comprises cooling means for cooling the container means with a selectable one of the two fluids, chamber dump and flush means for dumping and flushing the sample from the chamber, and drive cooling means for cooling at least a portion of the two paddle drive means.

A particularly novel and improved part of the present invention pertains to the apparatus for testing the static gel strength of the sample of material. This specific portion of the present invention, which is broadly encompassed in part by the aforementioned first paddle drive means and the static gel strength test control means, comprises the container; the paddle rotatably disposed in the chamber; force transferring means for transferring a force to the paddle so that the paddle rotates in response thereto; a support member; force sensing means for sensing a force exerted thereon; movement means for mounting the force sensing means on the support member and for linearly moving the force sensing means; and connector means, connected directly between the force sensing means and the force transferring means, for communicating a force to the force transferring means when the force sensing means moves linearly so that the paddle rotates. The apparatus further comprises set point means for setting a value related to a predetermined gel strength for the sample; comparison means, responsive to the force sensing means and the set point means, for determining when the force communicated through the connector means equals the value related to the predetermined gel strength; actuation means for actuating the movement means to commence moving the force sensing means; and timer means for indicating the time lapse between when the movement means commences moving the force sensing means and when the comparison means determines the force communicated equals the value related to the predetermined gel strength.

Therefore, from the foregoing, it is a general object of the present invention to provide a novel and improved multi-function apparatus for testing fluids. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 5 is a partial sectional view of a paddle and cap assembly associated with a container of the preferred embodiment of the present invention.

FIG. 6 is a partial sectional elevational view of a fluid-actuated hoist system of the preferred embodiment of the present invention.

FIG. 7 is a first elevational view of a portion of a static gel strength drive assembly of the preferred embodiment of the present invention.

FIG. 8 is another elevational view of a portion of the static gel strength drive assembly of the preferred embodiment of the present invention.

FIG. 9 is a side elevational view of a portion of a drain circuit and a high pressure circuit of a fluid system of the preferred embodiment of the present invention.

FIG. 10 is a front elevational view of a portion of the drain circuit and high pressure circuit of the preferred embodiment of the present invention.

FIG. 18 is a schematic circuit diagram of a master control portion associated with the control panel of the preferred embodiment of the present invention.

FIG. 19 is a schematic circuit diagram of a compressibility test control portion associated with the control panel of the preferred embodiment of the present invention.

FIGS. 20A–20C form a schematic circuit diagram of a thickening time test control system and a static gel strength test control system associated with the control panel of the preferred embodiment of the present invention.

FIG. 21 is a schematic circuit diagram of a temperature control, clock and strip chart recorder system associated with the control panel of the preferred embodiment of the present invention.

DETAILED DESCRIPTION OF THE PREFERRED EMBODIMENT

Figure 1:
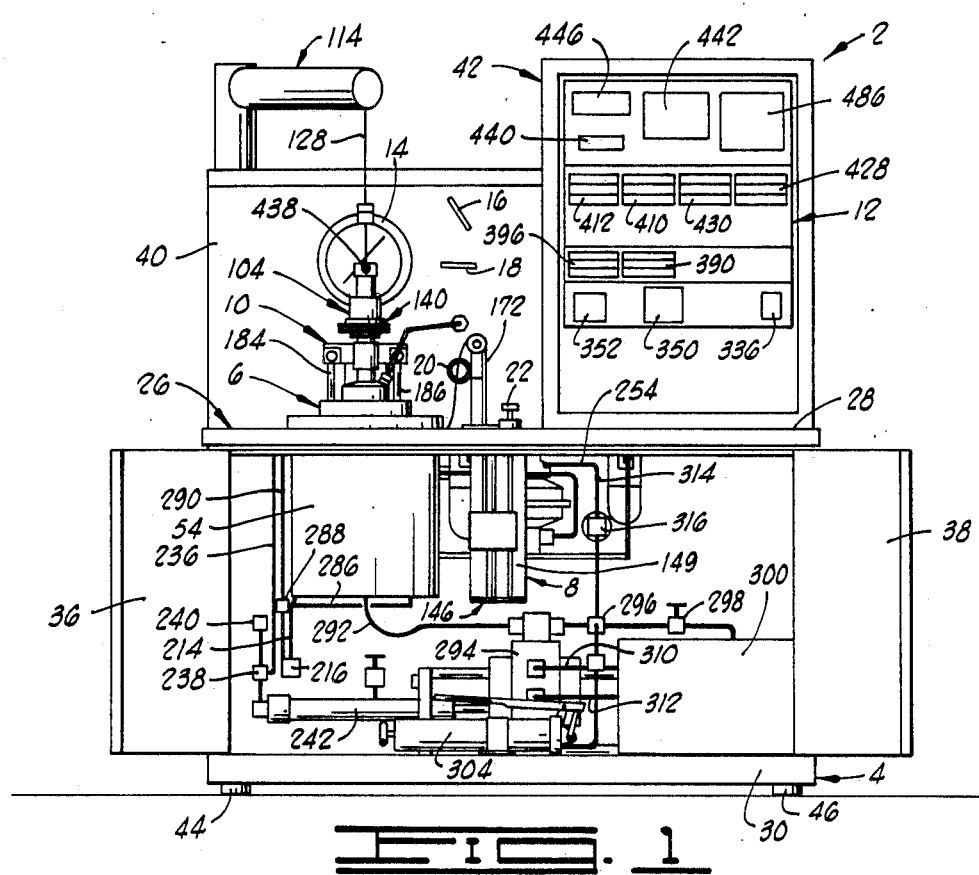
FIG. 1 is a front elevational view of the multi-function apparatus constructed in accordance with the preferred embodiment of the present invention, shown with its doors open.
Figure 3:
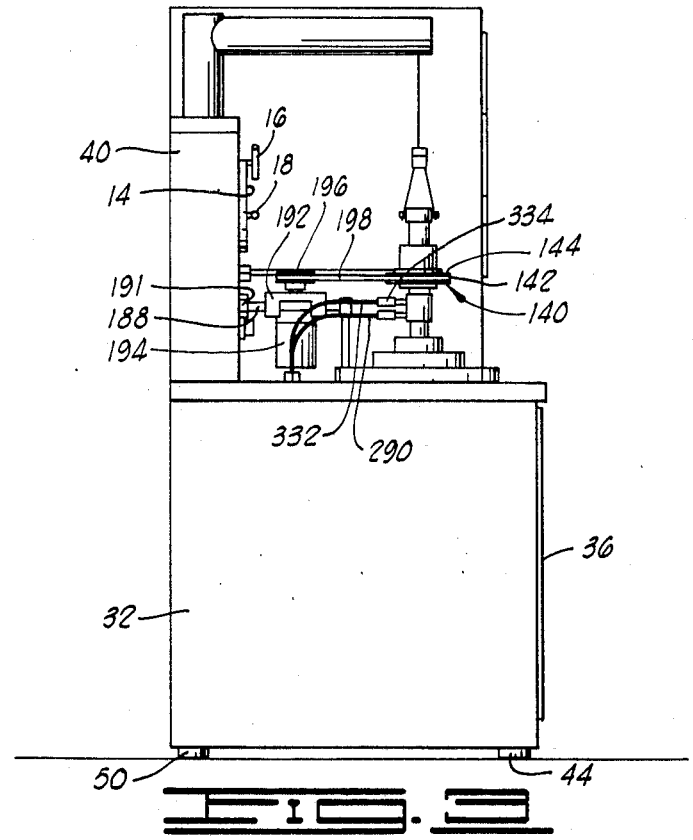
FIG. 3 is a side elevational view of the preferred embodiment of the present invention with the cabinet doors closed.
Figure 2:
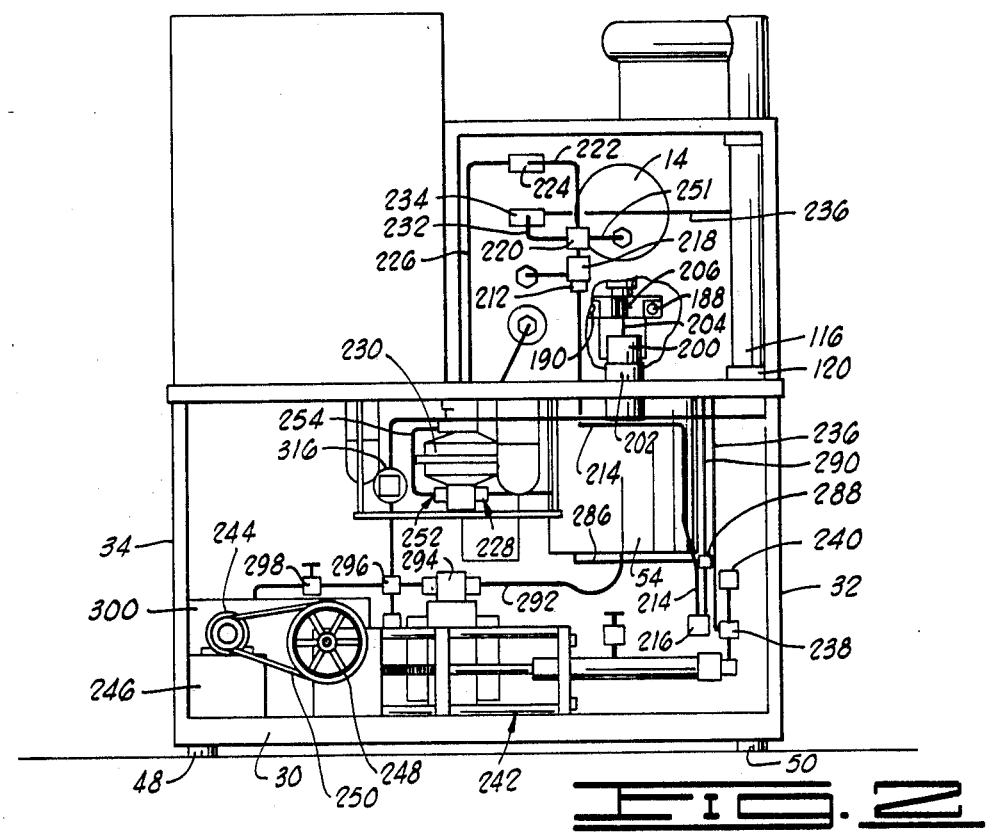
FIG. 2 is a rear elevational view of the invention shown in FIG. 1, but with the doors closed.
Figure 4:
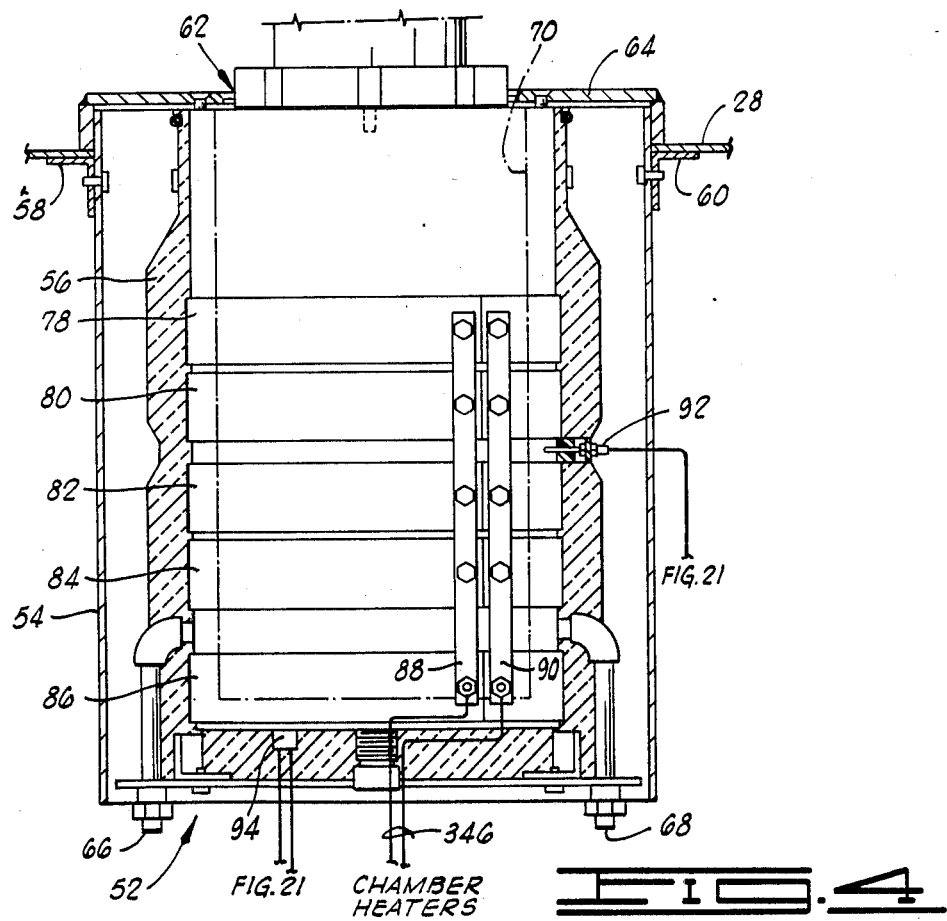
FIG. 4 is a partial sectional elevational view of the container of the preferred embodiment of the present invention.
Figure 11:
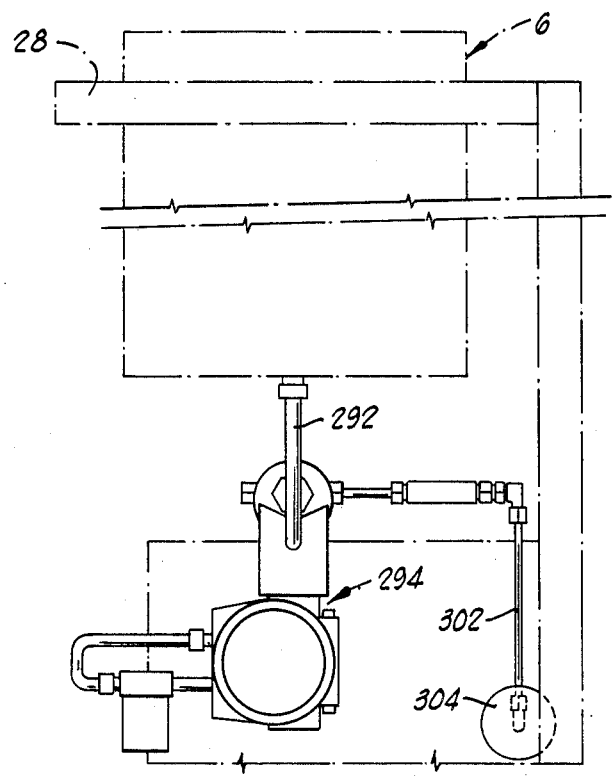
FIG. 11 is a side elevational view of a dump circuit of the fluid system of the preferred embodiment of the present invention.
Figure 12:
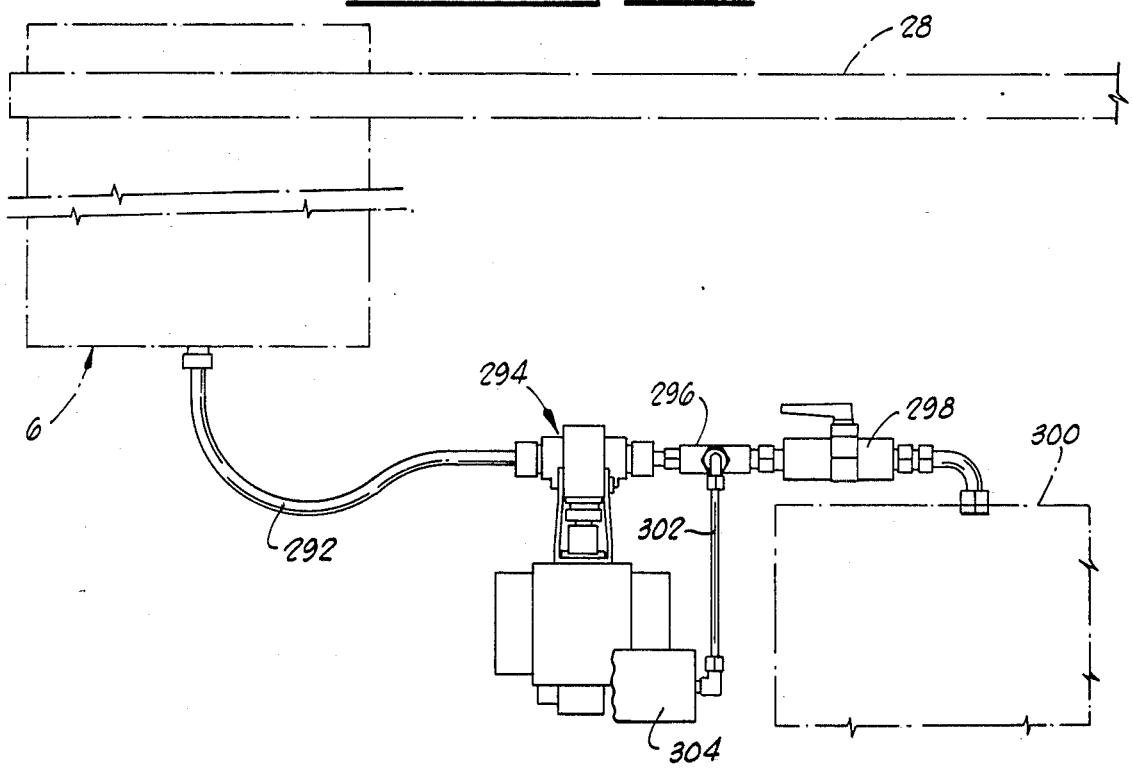
FIG. 12 is a front elevational view of the dump system of the preferred embodiment of the present invention.

The multi-function apparatus of the preferred embodiment of the present invention by which static gel strength, thickening time and compressibility tests can be selectably performed on a sample of a fluid, such as a cement slurry, is shown in FIGS. 1-3 and identified by the reference numeral 2. Generally, the apparatus 2 includes a transportable housing 4 in which test chamber equipment 6 is disposed. Operating on the test chamber equipment 6 are a static gel strength drive assembly 8 and a thickening time drive assembly 10. Disposed throughout the housing 4 (primarily in a lower compartment thereof) is a fluid system, including a pump with which the compressibility test is performed; these elements will be identified and more particularly described hereinbelow. Completing the general construction of the preferred embodiment of the apparatus 2 is the control means including a control panel 12, a pressure gauge 14 and manual valve and regulator controls 16, 18, 20, 22, 24 (FIGS. 13-14) to be further described hereinbelow.

The transportable housing 4 includes a stainless steel cabinet 26 having a top wall 28 defining a top shelf, having a bottom wall 30 defining a bottom shelf, and having two side walls 32, 34 extending perpendicularly between and interconnecting the top and bottom walls 28, 30. The walls 28, 30, 32, 34 define by their continuous inner surfaces an open compartment which can be closed from the front by a door 36 hinged to the side wall 32 and a door 38 hinged to the side wall 34. The back of the compartment is left open in the preferred embodiment as illustrated in FIG. 2. Extending perpendicularly above a part of the rear edge of the top wall 28 is a back wall 40 in which the pressure gauge 14 is suitably mounted. The controls 16, 18, 20, which are specifically handles attached to valves to be described hereinbelow, extend toward the front through the back wall 40. Located adjacent the back wall 40 and supported on the other portion of the top wall 28 is an electronics housing 42 in which the control panel 12 and its related electronic circuitry are contained. Attached to and extending below the bottom wall 30 are four supporting feet 44, 46, 48, 50. The feet 44-50 can be of any suitable construction, such as the stationery pads shown in the drawings or roller-type members so that the apparatus 2 can be easily moved along a floor. Housing 4 is otherwise compactly constructed for transportation to a field location for ready access by personnel for testing fluid samples.

With reference to FIGS. 1-5, the test chamber equipment 6 of the preferred embodiment will be described. The test chamber equipment 6 includes a high pressure, high temperature container 52 disposed within a metallic shield 54. A jacket 56 of suitable insulating material is disposed around the outside of the container 52. The container 52 and the shield 54 are suitably secured, such as by brackets 58, 60, to the top wall 28 through a hole or opening 62 defined therethrough. A protective shield member 64 is attached to the top of the container 52 and the shield 54 above the top wall 28. Cooling water lines 66, 68 communicate with the interior of the container 52.

The interior of the container 52 defines a chamber 70 into which the sample of a fluid to be tested is received. The inner surface defining the chamber 70 is coated with a nickel-based alloy to resist corrosion which might occur from the fluids when they are pressurized up to the high pressures that can be applied by the present invention. The contents within the chamber 70 can be pressurized through a pressurizing fluid inlet port 72 defined through a cap member 74 releasably secured to the container 52 by means of a retaining ring 76. In addition to being pressurized, the container 52 and the sample contained in the cavity 70 thereof can be heated by heating bands 78, 80, 82, 84, 86 which are energized through electrical bus bars 88, 90 in response to signals from the control panel 12 and related circuitry. The temperature is monitored and controlled in part through a wallmounted thermocouple 92 and a temperature limit switch 94.

The construction of the foregoing elements of the test chamber equipment 6 are of types as known to the art.

Forming another part of the test chamber equipment 6 is a paddle 96 (FIG. 5) having a support shaft 98, from which paddle wings 100 welded thereto extend, associated with a drive shaft 102 forming part of a magnetic drive mechanism of a type as known to the art and generally designated by the reference numeral 104 (FIG. 1). The magnetic drive mechanism 104 forms part of the two paddle drive means to be more particularly described hereinbelow. The paddle 96 can be constructed as a single unit or as a split paddle wherein one portion of the paddle rotates one revolution before engaging the other portion for thereafter driving the second portion as the first portion is further rotated. Located at the top of the paddle 96 is a slurry isolation plate 106 having a plurality of holes 108 formed therethrough for permitting communication between the slurry contained above and below the plate 106. The plate 106 allows a layer of static slurry to form as an isolating barrier between the slurry engaged by the paddle 96 and the pressurizing fluid maintained above the isolation plate 106. A biasing spring 110 extends between the isolation plate 106 and seal and support members 112.

To withstand the high pressures which can be applied within the chamber 70 of the container 52, the container 52 and the cap member 74 are constructed of heavy, durable material. To facilitate raising and lowering the heavy cap member 74 relative to the container 52, a fluid-actuated hoist means 114 is included as another portion of the test chamber equipment 6. A schematic representation of the preferred embodiment of the hoist means 114 is shown in FIG. 6. The hoist means 114 has a hollow scaffolding defined by an L-shaped tubular construction having a vertical element 116 and a horizontal element 118. A base structure 120 is bolted to the top wall 28 of the cabinet 26. Suitably retained within the hollow interior of the member 116 is a cylinder 122 having a piston, including a piston rod 124 and its connected piston head 126, slidingly disposed therein. The free end of the piston rod 124 has a cable 128 connected thereto by a suitable adapter member 130. The cable 128 extends over a pulley 132 rotatably connected near the junction of the members 116, 118 and over a pulley 134 rotatably connected at the free end of the member 118 as shown in FIG. 6. The cable 128 extends down from the pulley 134 for suitable attachment to the magnetic drive mechanism 104 as shown in FIG. 1.

Figure 13:
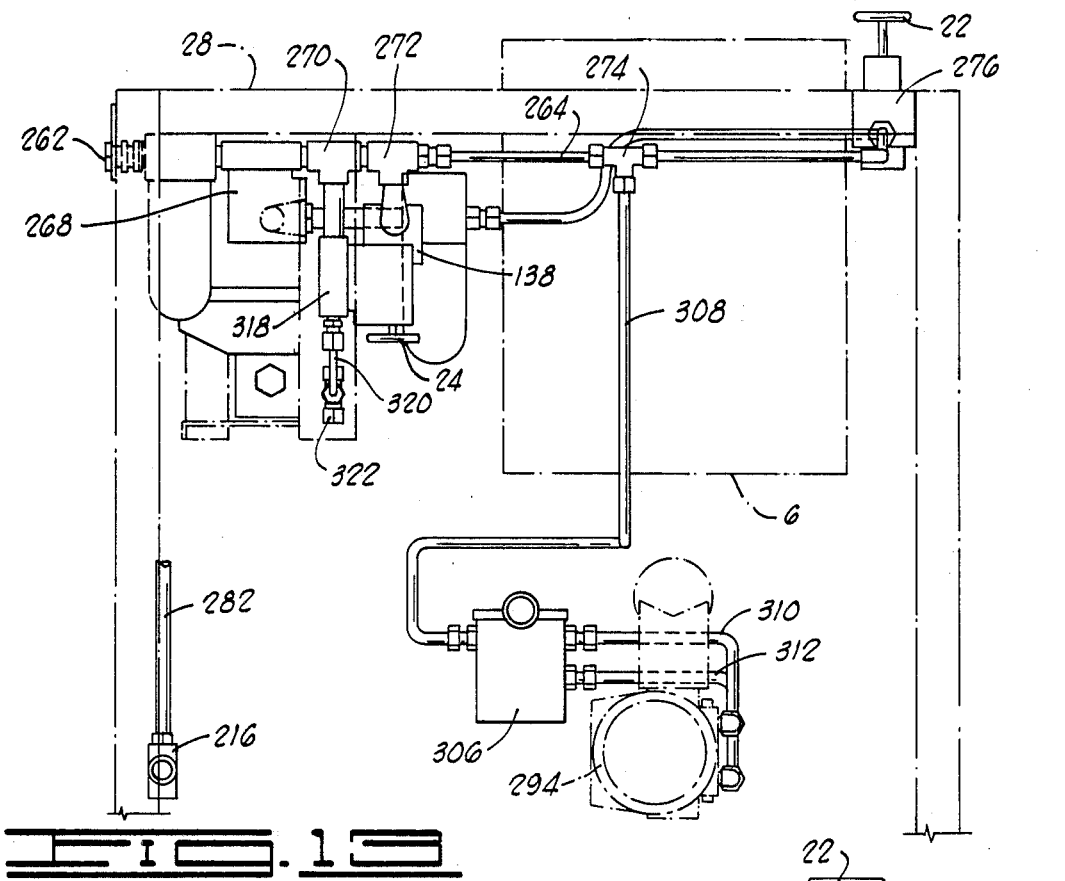
FIG. 13 is a side elevational view of an air inlet circuit of the fluid system of the preferred embodiment of the present invention.
Figure 14:
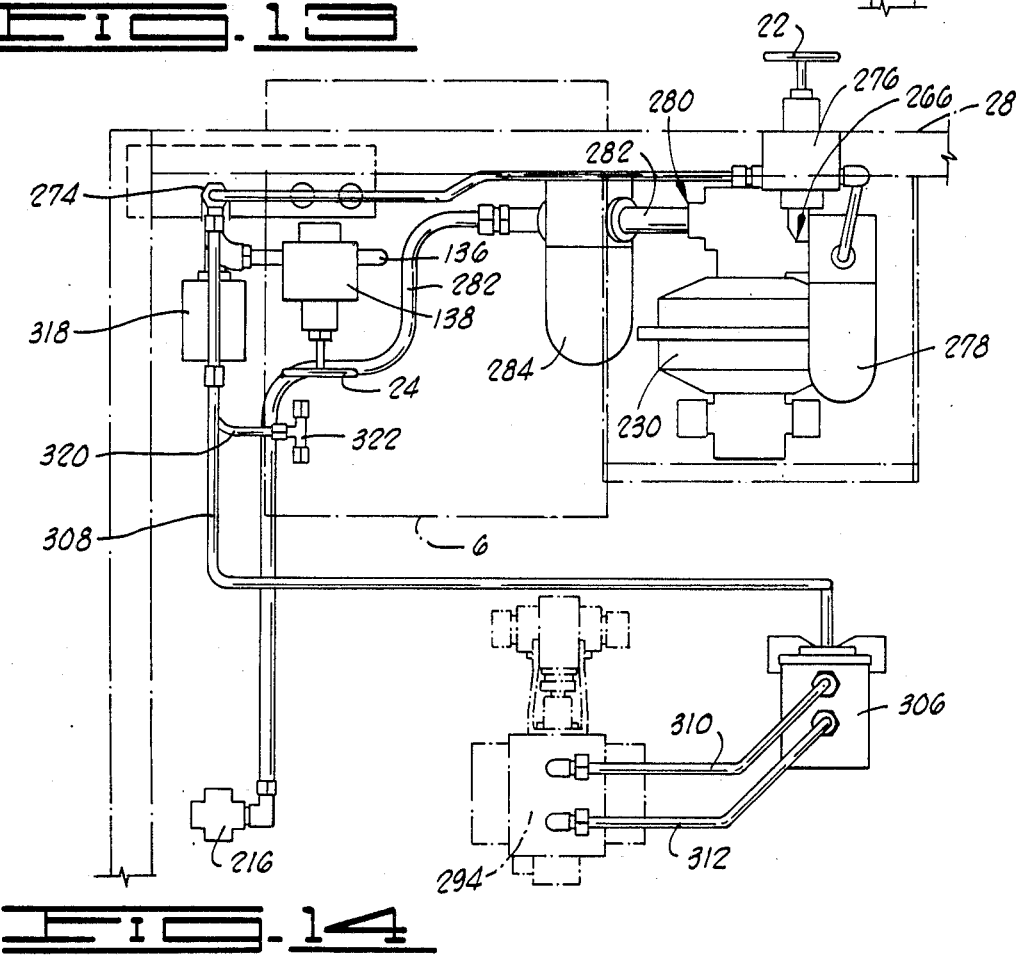
FIG. 14 is a front elevational view of the air inlet circuit of the preferred embodiment of the present invention.

To operate the cylinder and piston combination shown in FIG. 6, a suitable conduit 136 extends from the top of the cylinder 122 down through the hollow interior of the member 116 and through the base assembly 120 to an air regulator 138 shown in FIGS. 13 and 14. The air regulator 138 is controlled by actuating the control handle 24 which can also be seen in FIG. 1. The inlet to the air regulator 138 is suitably connected to a master solenoid of the air inlet circuit of the fluid system which will be further described hereinbelow. In the preferred embodiment the cylinder 122 is of a self-relieving type when the magnetic drive mechanism 104 and the associated cap member 74 are lowered.

With reference to FIGS. 1-3, 7 and 8, the preferred embodiment of the static gel strength drive assembly 8 will be described. Broadly, the assembly 8 includes force transferring means for transferring a force to the paddle 96 so that the paddle 96 rotates in response to the force. The assembly also includes a support member, force sensing means for sensing a force exerted on the force transferring means, movement means for mounting the force sensing means on the support member and for linearly moving the force sensing means, and connector means, connected directly between the force sensing means and the force transferring means, for communicating a force to the force transferring means when the force sensing means moves linearly so that the paddle 96 rotates.

In the preferred embodiment, the means for transferring a force generally includes the magnetic drive mechanism 104 and more particularly includes a sheave 140 (FIG. 1), having a rim with a circumferential groove 142 defined therearound and further having a notch 144 defined at a point along the circumference adjacent the groove 142, and also a magnetic coupling means for coupling the sheave and the paddle through the drive shaft 102 in a manner known to the art.

The support member in the preferred embodiment includes the top shelf 28 and a support bracket 146 suitably connected thereto. The bracket 146 is connected below an opening or hole 148 formed through the top wall 28. The bracket 146 has an elongated base 149 from which two end plates 150, 152 perpendicularly extend. The end plate 150 is connected to the underside of the top wall 28 by suitable fastening means such as screws 154, 156.

The force sensing means of the preferred embodiment includes a load cell 158 of a suitable type as known to the art.

The movement means of the preferred embodiment includes a lead screw 160 having a helical groove 162 defined therealong. The lead screw 160 is rotatably mounted or journaled in bearing mounts defined in the end plates 150, 152 as illustrated in FIGS. 7 and 8. The movement means also includes a carriage or load cell mount member 164 having a threaded channel defined therethrough for cooperatively engaging with the helical groove 162 of the lead screw 160. So that this cooperative engagement causes the carriage 164 to move linearly along the length of the lead screw 160, a guide rail or member 166 is supported at opposite ends in the end plates 150, 152 in parallel, spaced relationship to the lead screw 160. The carriage 164 rests on or receives the guide rail 166 so that when the lead screw 160 is rotated, the carriage 164 does not likewise rotate, but rather moves linearly. The movement means still further includes drive means for rotating the lead screw 160. In the preferred embodiment the drive means includes an electric motor 168 rotatably coupled to the lead screw 160 through a meshed gear set 170. The motor 168 is a variable speed motor and is controlled in response to signals from the control panel 12 as described hereinbelow. The motor 168 is suitably mounted on the support bracket 146.

The connector means of the preferred embodiment of the static gel strength drive assembly 8 includes a flexible line 172, such as a string, extending through the hole 148 for connection between the load cell 158 and the sheave 140. One end of the line 172 is connected directly to the load cell 158 through a suitable adapter connecting mechanism 174. The other end of the line 172 is connected to the sheave 140 by placing a knot in the end of the line 172 and securing the knot against the notch 144 disposed on the circumference of the sheave 140. The sheave 140 is then manually rotated so that a portion of the line 172 extending from the second end is received in the groove 142 and thereby wrapped around the sleeve 140. To suitably guide the flexible line 172 between its direct connection to the load cell 158 and the sheave 140, the connector means further includes a pulley 176 rotatably connected to a pulley support arm 178 which is attached to, and extends upwardly from, the top of the top wall 28 adjacent the hole 148.

The static gel strength drive assembly 8 also includes two limit switches 180, 182. The limit switch 180 is disposed near the end plate 150 to define an upper limit position to which the carriage 164 can be moved. It is to this position that the carriage 164 is moved by proper actuation of the motor 168 when the second end of the line 172 is retained in the notch 144 of the sheave 140 and wrapped in the circumferential groove 142. From this upper limit position, the carriage 164 can be moved to a lower limit position defined by the limit switch 182 disposed near the end plate 152. This direction of movement is generally effected in response to actuation of the motor 168 and the consequent rotation of the lead screw 160. During this direction of movement, the line 172 is unwrapped from the sheave 140, thereby rotating the sheave 140 and the paddle 96 coupled thereto through the magnetic drive mechanism 104. When either of the limit switches 180, 182 is engaged by the carriage 164, a control circuit to the drive motor 168 is opened, thereby inhibiting further operation of the motor 168 in that direction.

With reference again to FIGS. 1-3, the thickening time drive assembly 10 will be described. The assembly 10 includes a framework comprising vertical support members 184, 186 having their lower ends connected to the top wall 28 and having their upper ends connected to horizontal slide support members 188, 190. The ends of the members 188, 190 not connected to the vertical support members 184, 186 are connected to the back wall 40 by a suitable bracket 191. Slidably mounted on the support members 188, 190 is a drive motor slide mount 192. Attached at the center of the slide mount 192 is a variable speed motor 194 having a drive shaft upon which a sheave 196 is mounted for rotation with the shaft of the motor 194. The motor 194 is actuated in response to control signals from the control panel 12 and its related electronics as more particularly described hereinbelow. The sheave 196 is coupled with the sheave 140 of the magnetic drive mechanism 104 by a flexible drive belt 198. Appropriate tension is maintained on the belt 198 by a tensioning mechanism including a tensioning weight 200 slidably received in a weight receiving cup 202 connected to the top wall 28 through an opening defined therein behind the back wall 40. The weight 200 is attached to the slide mount 192 by a flexible cable 204 extending from the weight 200 over a pulley 206, attached to the back wall 40, to a point of connection on the slide mount 192.

With reference to FIGS. 1-3, 9-10 and 13-16, the pressurizing circuit forming a part of the fluid system of the preferred embodiment of the present invention will be described. The pressurizing circuit applies a pressure to the sample within the chamber 70. This pressure is established through a pressurizing fluid flowed into the chamber 70 through the inlet port 72. In the preferred embodiment the pressurizing fluid is water; however, other types of fluids, such as air or nitrogen, can be used. FIGS. 9 and 10 show that the pressurizing circuit includes a conduit 208 extending through couplings 210, one element of which is a quick disconnect type of coupling, to a port of a rupture disk 212, thereby maintaining the rupture disk 212 in continuous fluid communication with the inlet 72 and thus the chamber 70. This is important for safety reasons so that any overpressure condition occurring within the chamber 70 will be properly vented through the rupture disk 212 and a drain line conduit 214 extending from another port of the rupture disk 212. The conduit 214 connects to a drain outlet member 216 of a suitable type as known to the art, which outlet member 216 is suitably mounted on the cabinet 26 of the preferred embodiment. The connection of the conduit 208 to the rupture disk 212 is made through a joint member 218 having another port connected to another coupling joint 220. One port of the joint member 220 is connected through a conduit 222 to a valve 224 having a valve stem connected to the control handle 16. The valve 224 is also connected through a conduit 226 to a pumped fluid outlet 228 of a pump 230. In the preferred embodiment the pump 230 is an air pump such as a Sprague pump.

Another port of the joint member 220 is connected through a conduit 232 to another valve 234 having a valve stem connected to the control handle 18. The valve 234 is connected through a conduit 236 to a connector 238 interconnecting the valve 234 with a pressure transducer 240 and the plunger end of a pressure/volume pump 242. The pump 242 is of any suitable type as known to the art for withdrawing a measurable volume of fluid from the chamber 70 when the valve 234 is open and the pump 242 is appropriately actuated in response to control signals from the control panel 12 and its associated electronics as more particularly described hereinbelow. The pump 242 is driven by such control signals through operation of a motor 244 mounted on a support frame 246 attached to the bottom wall 30 of the cabinet 26 and coupled to a drive wheel or pulley 248 of the pump 242 through a drive belt 250.

The joint 220 has still another port which is connected to the pressure gauge 14 through a conduit 251 so that the pressure gauge 14 is in continuous communication with the chamber 70. That is, the valves 224, 234 can isolate the pumps 230, 242, respectively, from the chamber 70, but they cannot isolate either the gauge 14 or the rupture disk 212 from the chamber 70.

Figure 15:
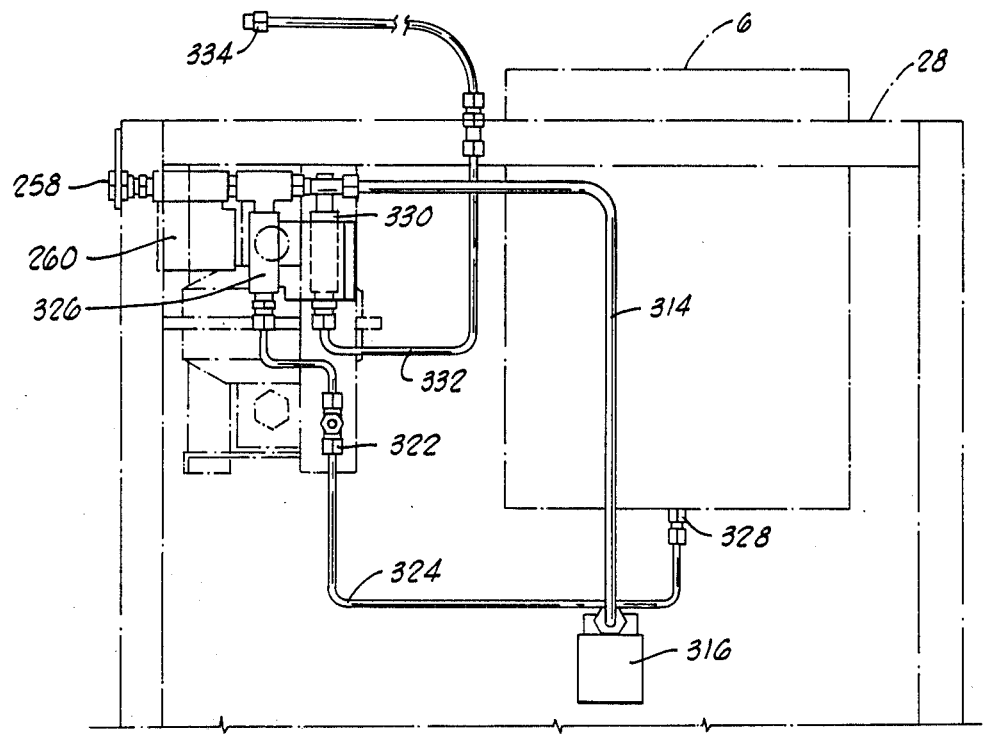
FIG. 15 is a side elevational view of a water inlet circuit of the fluid system of the preferred embodiment of the present invention.
Figure 16:
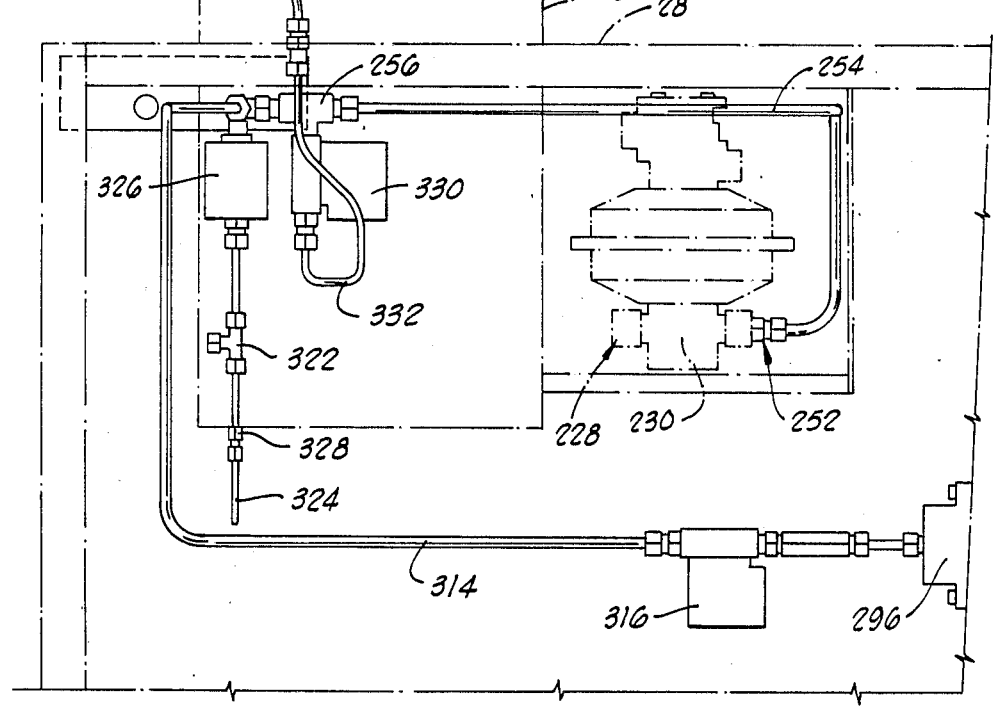
FIG. 16 is a front elevational view of the water inlet circuit of the preferred embodiment of the present invention.

FIGS. 15 and 16 show the water inlet circuit of the fluid system through which the pressurizing fluid is provided to a driven or pumped fluid inlet 252 of the pump 230. This portion of the system includes a conduit 254 extending from the inlet 252 to coupling members 256 which are ultimately connected to a master fluid inlet connector 258 through an electrically controlled master water solenoid valve 260 (FIG. 15). Thus, when the solenoid valve 260 is open, a fluid from a fluid source (such as a common source of water available at a tap of a municipal water system) connected to the connector 258 flows through the conduit 254 for being pumped by the pump 230 when the pump 230 is properly actuated.

To actuate the pump 230, which in the preferred embodiment is an air-actuated pump, air from a suitable air source connected to master fluid inlet connector 262 of the air inlet circuit (FIGS. 13 and 14) is provided through a conduit 264 extending between the connector 262 and a drive inlet 266 of the pump 230. Disposed within the conduit 264 are an electrically actuated master air solenoid valve 268, T-connectors 270, 272, 274, an air regulator 276 manually actuated by the control knob 22, and an air line lubricator 278. The driving fluid (i.e., air in the preferred embodiment) flows through the pump 230 and out a driving fluid outlet 280 connected through a conduit 282 to the drain outlet member 216. The conduit 282 has an oil removal filter 284 disposed therein. The connector 272 couples with the air regulator 138 of the air hoist system.

Both of the solenoid valves 260, 268 are controlled in response to signals from the control panel 12 and its associated electronics as subsequently described.

Again with reference to FIGS. 9 and 10, the cooling fluid drain circuit of the overall fluid system of the preferred embodiment will be described. Extending from a selectable one of the cooling lines 66, 68 of the container 52 is a drain conduit 286 which passes through a T-connector 288 to a connection with the outlet drain member 216. Also connected to the T-connector 288 is a conduit 290 extending from the magnetic drive mechanism 104.

With reference to FIGS. 11-16, the dump and flush circuit of the overall fluid system of the preferred embodiment will be described. This system is used for dumping the sample from the chamber 70 and for flushing out the chamber 70. The chamber 70 is connected by a conduit 292 to an air actuated ball valve 294. The ball valve 294 is connected through a coupling 296 and a manually actuated ball valve 298 to a reservoir including a dump bucket contained within an enclosure 300 mounted on the bottom wall 30 of the cabinet 26. The connector 296 is also connected, by a conduit 302, to a grease gun 304 so that the valve 294 can be filled with grease to prevent abrading action between the dumped sample and the ball of the valve 294 when the ball is moved from its closed to its open position.

To actuate the ball valve 294, an electric solenoid 306 shown in FIGS. 13 and 14 is actuated from the control panel 12. The solenoid valve 306 communicates air from a conduit 308 connected to the T-connector 274 to a selectable one of a conduit 310 and a conduit 312 connected to the operating inputs of the valve 294.

To flush the dump line and the chamber 70, the connector 296 is also connected to a conduit 314, connected to the connector 256 of the water inlet line coming from the connector 258 as shown in FIGS. 15 and 16. Disposed in the conduit 314 is another electrically actuated solenoid valve 316 which is actuated in response to a control signal provided from the control panel 12.

With reference to FIGS. 13-16, the cooling circuit of the fluid system will be described. One portion of the cooling circuit provides for air cooling, and the other portion of the cooling circuit provides for water cooling of the container 52. The air cooling portion is shown in FIGS. 13 and 14 as including an electrically actuated solenoid valve 318 connected to the T-connector 270. The solenoid valve 318 is also connected, by means of a conduit 320, to a T-connector 322. FIGS. 15 and 16 show that the T-connector 322 also forms part of a conduit 324 connecting another electrically actuated solenoid valve 326 to a coolant inlet connector 328 communicating with the other of the lines 66, 68 not connected to the drain conduit 286. The solenoid valves 318, 326 are controlled from suitable switches contained in the control panel 12 as described hereinbelow. Depending upon which of the solenoid valves 318, 326 is open, either air or water flows into the inlet 328 for circulation through the container 52 and for subsequent draining through the drain line 286 shown in FIGS. 9 and 10.

Still another portion of the fluid system is the drive cooling circuit which includes an electrically actuated solenoid valve 330 connected to the T-connector 256 of the water inlet system shown in FIGS. 15 and 16. The solenoid valve 330 is connected through a conduit 332 to an inlet 334 of the magnetic drive mechanism 104. When the solenoid valve 330 is opened, which occurs in response to a control signal from the control panel 12, water circulates through the magnetic drive mechanism 104 and thereafter flows out through the drain line 290 shown in FIGS. 9 and 10. This construction utilizing the solenoid valve 330 is in lieu of a manually controlled valve which would be functionally located where the solenoid valve 330 is, but which would be actuated by the handle 20 shown in FIG. 1; therefore, in the embodiment utilizing the solenoid valve 330, the handle 20 can be deleted.

Figure 17:
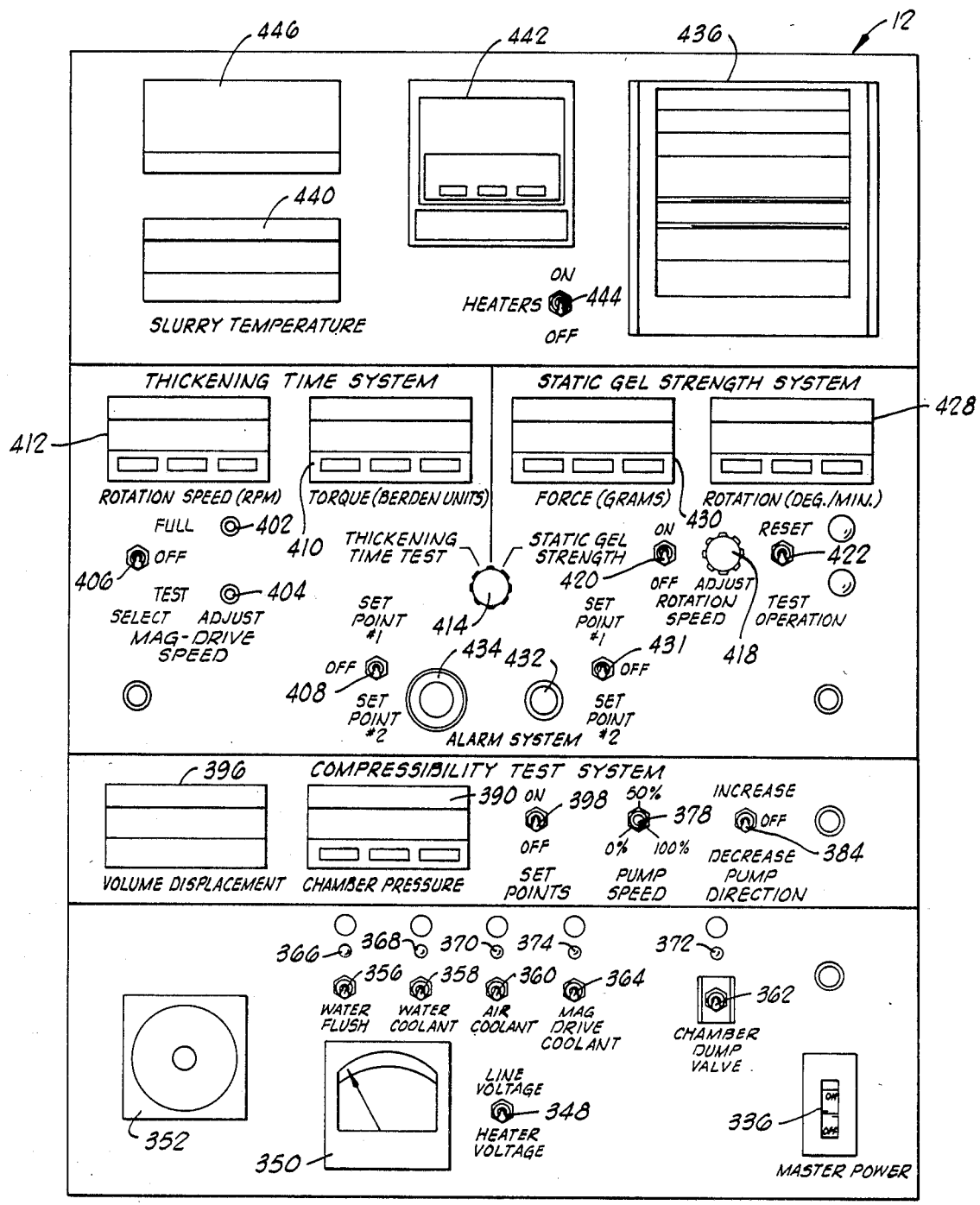
FIG. 17 is an enlarged view of a control panel associated with a cabinet of the preferred embodiment of the present invention.

With reference to FIGS. 17 and 18, the master control portion of the control panel 12 will be described. A master electrical power on/off switch 336, through which the primary energization is provided to the apparatus 2, is mounted on the face of the control panel 12. In the preferred embodiment the primary power comes from a 240-vac, 60-hertz service line connected through a plug 338. This voltage level is reduced to 120-vac through a transformer 340.

When the master switch 336 is closed, a relay 342 is energized to close relay contacts interconnecting the plug 338 with a solid state switch 344 through which power is provided to the heater bus bars 88, 90 over conductors 346 under control of a temperature controller subsequently described with reference to FIG. 21. The voltage on either the heater conductors 346 or on the primary line can be monitored by appropriately setting a switch 348 connected to a voltmeter 350.

When the master on/off power switch 336 is closed, a cooling fan 352 is activated and a regulated DC power supply 354 is energized to provide a DC voltage. Closing of the switch 336 also provides an operating voltage across switches 356, 358, 360, 362, 364. The switch 356 is the water flush control switch used to control the solenoid valve 316; the switch 358 is the water coolant control switch used to control the solenoid valve 326; the switch 360 is the air coolant control switch used to control the solenoid valve 318; the switch 362 is the chamber dump valve control switch used to control the solenoid valve 306; and the switch 364 is the drive coolant control switch used to control the solenoid valve 330 (the function of the switch 364 is in lieu of the handle 20 shown in FIG. 1). When any of the switches 356, 358, 360, 362, 364 is closed, a respective light 366, 368, 370, 372, 374 is illuminated.

With reference to FIGS. 17 and 19, the compressibility test control means associated with the control panel 12 will be described. The compressibility test control means controls the operation of the pump 242 in withdrawing a portion of the sample from the chamber 70 for determining pressure and volume differentials which can be used to compute compressibility. For properly controlling the pump motor 244, which in turn controls the pump 242, a motor controller 376 of a type as known to the art is included in the control circuit as shown in FIG. 19. A potentiometer 378 is connected to the motor controller 376 for setting the desired speed at which the pump 242 is to be operated. To stop movement of the pump when the plunger within the pump reaches either its maximum extended or maximum retracted limits, limit sensing switches 380, 382 are suitably mounted on the pump 242 for detecting the end positions of the plunger. When an end position is reached, the respective one of the switches 380, 382 is opened which breaks the circuit from the motor controller 376 to the motor 244 running through a pump direction switch 384. Positioning of the pump direction switch 384 determines the direction which the plunger of the pump 242 will be driven. Relay switches 386, 388 are also disposed in these circuits shown in FIG. 19. The function of the relay switches 386, 388 is to open these circuits, and thereby stop movement of the pump 242, when a pressure set point is reached. The pressure set point is entered through a chamber pressure selection and display device 390 of a type as known to the art. The device 390 responds to the pressure transducer 240 and compares it to an entered, preselected pressure set point. When the actual pressure detected by the pressure transducer 240 equals the set point pressure value, the device 390 appropriately controls the relay switches 386, 388 to open their respective circuits to break the circuit between the motor controller 376 and the motor 244.

To determine the position of the plunger within the pump 242, and thereby to determine the displacement volume of the withdrawn portion of the sample from the chamber 70, a linear transducer, represented as a rheostat 392 in FIG. 19, is suitably attached to the pump 242. The rheostat 392 is changed as the plunger of the pump 242 moves, thereby generating a signal which is provided to a signal conditioning circuit 394 of a suitable type for converting the rheostat signal into a signal suitable for driving a displacement volume display 396.

In operation, the chamber pressure set point is entered through the device 390, the pump speed is set by the potentiometer 378 and the direction of the pump is set by the switch 384. A set point on/off switch 398 is then closed, which permits opening of the normally closed relays 386, 388 when the pressure set point is reached, whereupon the motor controller 376 is disconnected from the motor 244. The motor controller 376 is also disconnected from the motor 244 when the appropriate limit switch is opened by the pump plunger reaching a limit of travel. Because the relays 386, 388 are normally closed, the pump can be operated even with the switch 398 in its off position. During this operation the pressure detected by the pressure transducer 240 is displayed through the chamber pressure selection and display device 390 and the volume of the portion of the sample received in the plunger cylinder of the pump 242 is displayed in the displacement volume display 396. From the chamber pressure and displacement volume readings, one can calculate the compressibility utilizing equations known to the art.

With reference to FIGS. 17 and 20A–C, the thickening time test control means associated with the control panel 12 will be described. The thickening time test control means controls the operation of the motor 194 in driving the magnetic drive mechanism 104 and the paddle 96 via the coupling belt 198. The speed of the motor 194 is controlled by a suitable motor controller 400 in response to the setting of two potentiometers 402, 404 which are switchably connectible to the motor controller 4 through a triple-pole double-throw switch 406.

The motor 194 is operated during a test until a preselected torque value is reached. Either of two predetermined torque values can be selected by means of a switch 408 connected to a torque display and selecting device 410 of a type as known to the art. The torque values selected and entered into the device 410 are chosen in a manner as known to the art, such as from standard API tables. As the motor controller is operating the motor 194, the rotation speed and torque, both as detected through the current from the motor controller 400 driving the motor 194, are displayed in a rotation speed display device 412 and the torque display and selecting device 410. The thickening time test control means is switchably selectable by a selector switch 414.

Figure 20A:
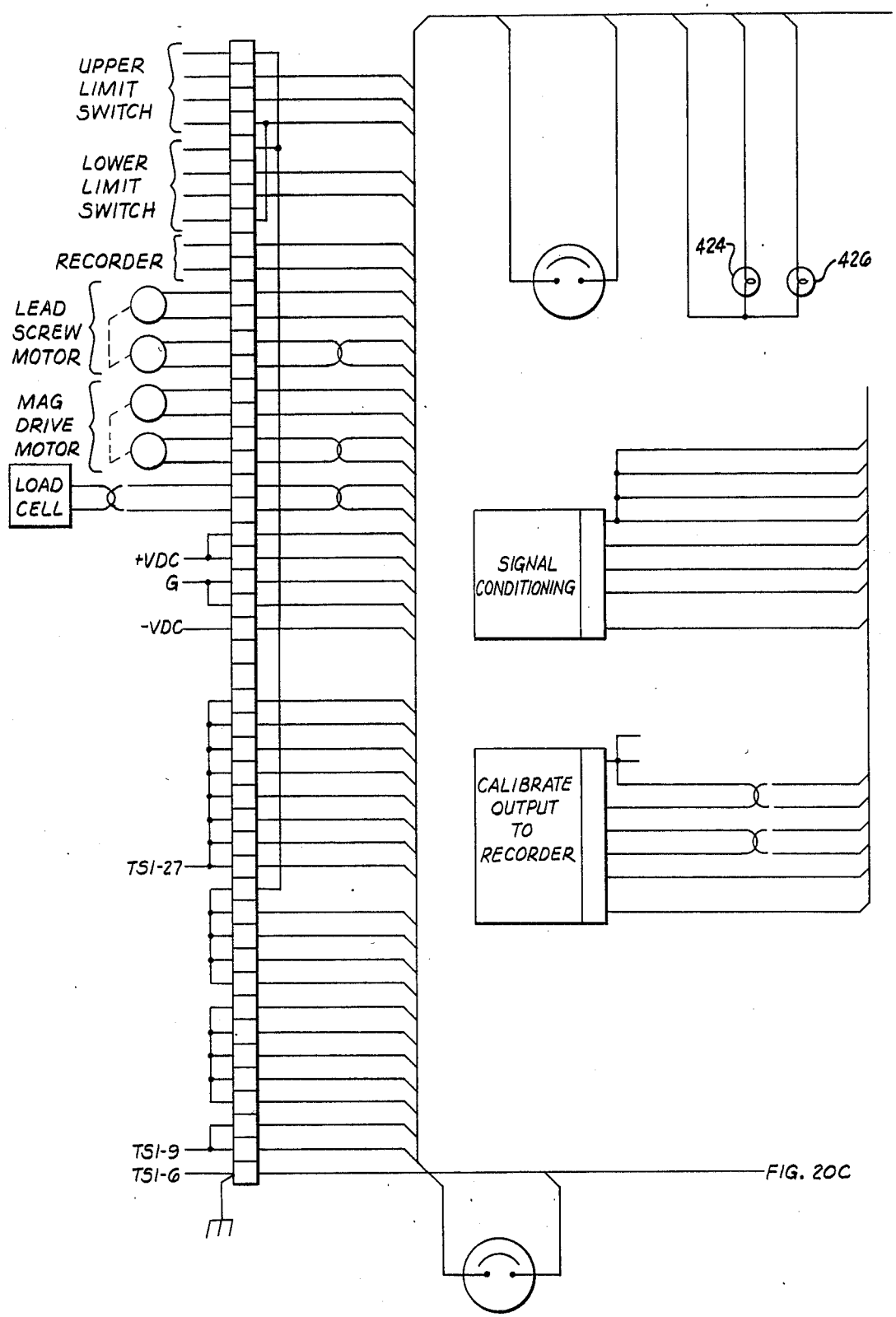
Figure 20B:
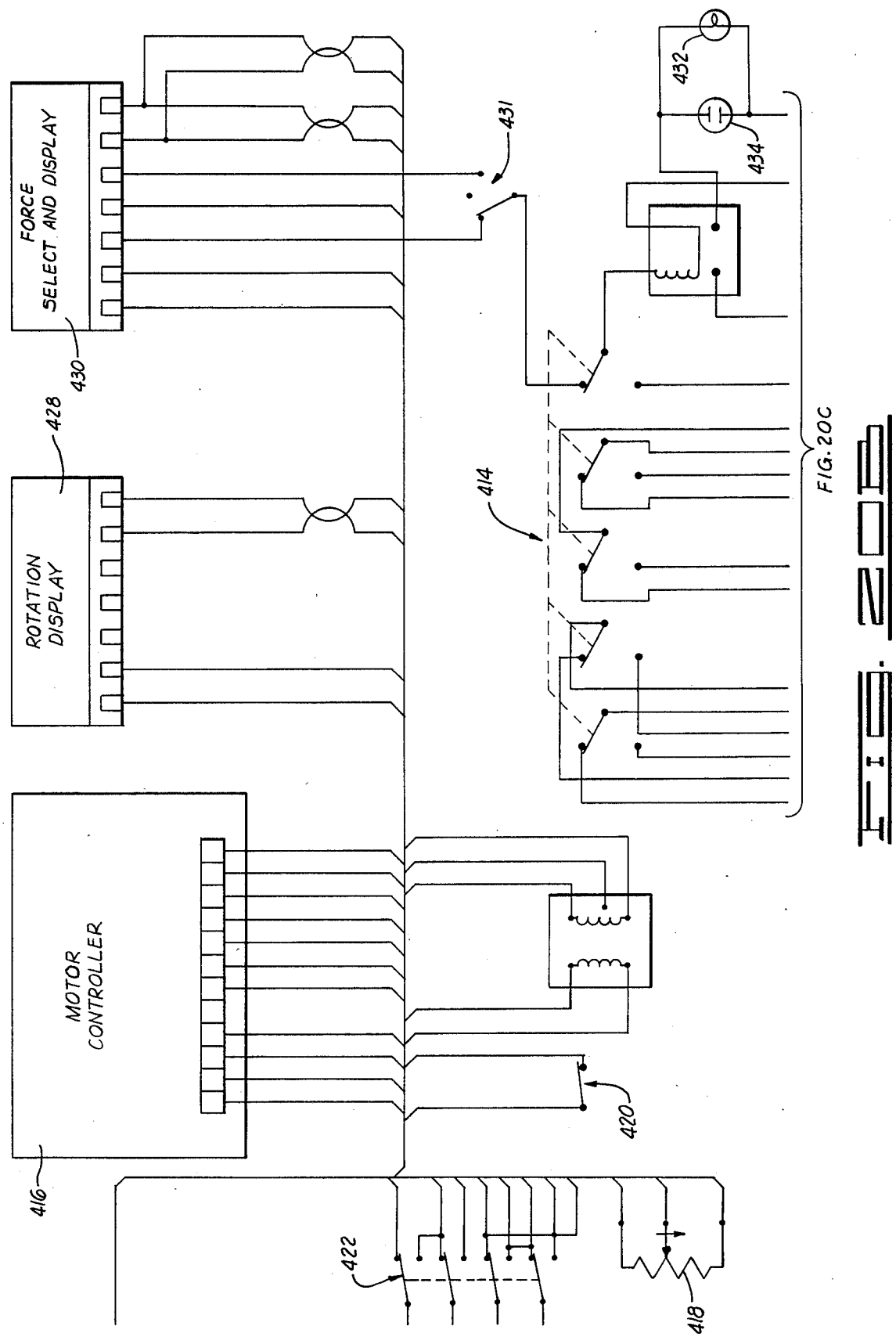

By appropriately positioning the switch 414, the static gel strength test can be run using static gel strength test control means associated with the control panel and also shown in FIGS. 17 and 20. The static gel strength test control means also includes a motor controller, designated in FIG. 20B by the reference numeral 416. The speed at which the motor controller 416 operates the motor 168 of the static gel strength assembly shown in FIGS. 7 and 8 is controlled by a potentiometer 418. Generally, the movement means of the static gel strength test system is actuated, and more specifically, the motor controller is switched on and off, by means of a switch 420. The reset/test operation switch 422 is used to control which direction the motor controller 416 drives the motor 168, and thereby moves the carriage 164 along the lead screw 160. When the carriage 164 reaches one of its limits, a respective one of upper and lower limit indicating lights 424, 426 (FIG. 20A) is illuminated and the motor controller 416 is disconnected from the motor 168 in response to the respective limit switch 180, 182 being opened.

When the motor controller 416 is operating the motor 168, the rotational speed of the motor is displayed in a suitable display device 428, which is responsive to the current provided by the motor controller 416. The force exerted on the load cell 158 through the line 172 is displayed in a force display and selection device 430. The force exerted on the load cell 158 is proportional to the input torque which equals the output torque applied to the paddle plus the coupling losses through the magnetic drive mechanism; therefore, the detected force is related to the static gel strength to which the output torque is proportional. The device 430 is also used to select two predetermined set points representative of or related to a predetermined static gel strength against which the force signal from the load cell 158, representative of the actual gel strength, is compared. When the selected predetermined set point and the detected force are equal, an alarm light 432 and an alarm buzzer 434 are activated. The alarm devices 432, 434 are also activated when the thickening time test control means has been selected through the switch 414 and the detected and preselected torques are equal. One of the two set points is selected through operation of a switch 431. As with the set points for the thickening time test system, the values of the set points for the static gel strength test system are chosen in a manner known to the art.

Whichever one of the thickening time test control means or static gel strength test control means is selected through the switch 414, the monitored torque (thickening time test) or force (static gel strength test) is provided to a strip chart recorder 436 shown in FIGS. 17 and 21.

The recorder 436 shown in FIGS. 17 and 21 is of a suitable type as known to the art. In addition to recording the parameter of the selected thickening time test system or the static gel strength test system, the recorder 436 records the slurry temperature detected by a thermocouple 438 attached at the top of the magnetic drive mechanism 104 (FIG. 1). The recorder 436 also records the chamber wall temperature detected by the thermocouple 92. The slurry temperature is also displayed in a suitable display meter 440. The heat applied to the chamber 52, which is detected by monitoring the aforementioned two temperatures, is controlled by a temperature control device 442 of a type as known to the art. The controller 442 is switchably connected through a switch 444 to the solid state switch 344 represented in both FIGS. 18 and 21. The circuit between the controller 442 and the switch 344 includes the temperature limit switch 94 also shown in FIG. 4. The switch 94 acts as a thermostatic control to insure that the heaters are not energized when the temperature detected by the temperature limit switch reaches the predetermined value at which the switch 94 is responsive, which in the preferred embodiment is not greater than 600° F.

Also contained on the control panel 12 as shown in FIGS. 17 and 21 is a clock or timing device 446 of a type as known to the art. The clock has suitable starting, stopping and resetting controls as known to the art which can be manually actuated by the operator of the present invention in correspondence with the starting of either the thickening time test or static gel strength test and the corresponding termination of those tests as indicated by the sounding of the alarm 434 and the illumination of the alarm lamp 432. Therefore, the operator can easily determine the amount of time it takes the selected sample to reach the preselected thickening or static gel strength representative values.

In operation, the master on/off switch is placed in its on position to energize the apparatus 2. The switches 356, 358, 360, 362, 364 are placed in the appropriate positions depending upon whether cooling, dumping, or flushing functions are to be performed. The switch 348 is placed in either of its desired positions to monitor either the line voltage or the heater voltage. Thereafter, one of the compressibility, thickening time, or static gel strength tests can be performed. Only one of the thickening time and the static gel strength tests can be performed at one time; however, the compressibility test can be performed with either of the other two tests. The procedure of the compressibility test has been previously described; therefore, only the more detailed operations of the thickening time test system and the static gel strength test system will be described.

Initial steps include lifting the cap off the container 52 and placing a sample of the material to be tested into the chamber 70. The temperature and pressure are brought up to preselected values with the aforementioned controls in a manner readily apparent to those skilled in the art. The thickening time test is performed by entering the desired set points through the selection device 410 and selecting one of the two predetermined set points by appropriately setting the switch 408. The potentiometers 402, 404 are set, if they have not already been set, to properly control the motor controller 400. The switch 406 is then moved into the test position; this causes the motor controller 400 to energize the motor 194 which turns the sheave 140 of the magnetic drive mechanism 104 and the paddle 96 coupled thereto. The speed at which the paddle 96 is driven is sufficiently high to agitate the sample of material contained in the chamber 70. This agitation may prevent gelling, but it does not prevent the cement slurry of the preferred embodiment sample from setting up. As the slurry sets up, the torque on the paddle 96 increases. When this torque, represented by the current of the motor controller 450, equals the selected set point value, the alarms 432, 434 are energized and the time of the test is noted as previously described.

By changing the position of the switch 414, the static gel strength test can be performed. With the switch 414 suitably positioned, and the drive belt 198 removed from the sheave 140 after the sample has been sufficiently agitated (such as by the method just described), the end of the line 172 is placed in the notch 144 and the sheave 140 manually rotated to wind a portion of the line 172 around the circumferential groove 142 of the sheave 140. This wrapping is done until the carriage 164 has been moved to its upwardmost position, thereby engaging the limit switch 180. The values representing the predetermined static gel strength are entered through the device 430 and one of the two values selected by means of the switch 431. The potentiometer 418 is set to define the speed at which the motor controller 416 is to operate the motor 168. The switch 422 is placed in the test operation position so that the motor controller 416 will drive the motor 168 in a direction whereby the carriage 164 will be caused to move down the lead screw 160 toward the lower limit switch 182. With the system thus preset, the switch 420 is switched to its on position whereby the carriage 164 begins to move slowly down the length of the lead screw 160. In the preferred embodiment wherein a sample of cement slurry is tested, the carriage 164 is moved so that the line 172 pulls and rotates the sheave 140 whereby the paddle 96 is turned at a speed within the range of approximately 0.2 to 2.0 degrees per minute, a rate which does not agitate the slurry sample and leaves it in a relatively static state. In such a static state, the slurry begins to gel. Gelling increases the force on the line 172, which force is detected by the load cell 158. When this force equals the selected predetermined value, the alarms 432, 434 are actuated and the time is noted as previously described.

The individual elements described hereinabove are of types known to the art; therefore, more detailed descriptions of them or of their operation are not necessary for a complete understanding of the present invention.

Thus, the present invention is well adapted to carry out the objects and attain the ends and advantages mentioned above as well as those inherent therein. While a preferred embodiment of the invention has been described for the purpose of this disclosure, numerous changes in the construction and arrangement of parts can be made by those skilled in the art, which changes are encompassed within the spirit of this invention as defined by the appended claims.

What is claimed is:

1. An apparatus for testing a sample of material, comprising:
a cabinet;
container means, having a chamber defined therein, for receiving the sample of material in said chamber, said container means connected to said cabinet;
a paddle rotatably disposed within said chamber;
first paddle drive means, connected to said cabinet, for rotating said paddle at a first speed so that the sample is maintained relatively static within said chamber despite said paddle rotating at said first speed;
second paddle drive means, connected to said cabinet, for rotating said paddle at a second speed so that the sample is agitated within said chamber by said paddle rotating at said second speed;
heater means, connected to said container means, for heating the sample within said chamber;
pressurizing means, mounted on said cabinet, for applying a pressure to the sample within said chamber, said pressurizing means including pump means for extracting a measurable quantity of the sample from said chamber, said pump means having a plunger movably disposed therein;
static gel strength test control means, mounted on said cabinet, for controlling said first paddle drive means, including:
first speed control means for setting an angular speed at which said first paddle drive means rotates said paddle;
first set point means for selecting a set point representative of a predetermined static gel strength;
first sensor means for sensing an input force applied by said first paddle drive means to rotate said paddle in response to said first speed control means; and
means, responsive to said first set point means and said first sensor means, for indicating when the sensed input force equals the set point representative of the predetermined static gel strength;
thickening time test control means, mounted on said cabinet, for controlling said second paddle drive means, including:
second speed control means for setting a rotational speed at which said second paddle drive means rotates said paddle;
second set point means for selecting a set point representative of a predetermined consistency;
second sensor means for sensing a parameter proportional to the torque applied by said second paddle drive means in response to said second speed control means; and
means, responsive to said second set point means and said second sensor means, for indicating when the sensed parameter equals the set point representative of the predetermined consistency;
compressibility test control means, mounted on said cabinet, for controlling said pump means, including:
third speed control means for setting a speed at which said plunger of said pump means moves;
directional control means for controlling the direction said plunger of said pump means moves;
third sensor means for sensing a pressure of the measurable quantity of fluid extracted by said pump means;

fourth sensor meas for sensing a volume of the measurable quantity of fluid extracted by said pump means; and display means, responsive to said third and fourth sensor means, for displaying the sensed pressure and volume; and temperature control means, mounted on said cabinet, for controlling said heater means to heat said sample to a selectable temperature.

2. An apparatus as defined in claim 1, wherein:
said temperature control means includes:
fifth sensor means, connected to said container means, for sensing the temperature of said container means; and
sixth sensor means, connected to said container means, for sensing the temperature of the sample received in said container means; and
said apparatus further comprises strip chart recorder means, mounted on said cabinet, for visually recording the temperatures sensed by said fifth and sixth sensor means and for visually recording a parameter in response to a selectable one of said first and second sensor means.

3. An apparatus as defined in claim 1, wherein said first paddle drive means includes:
a support member attached to said cabinet;
a lead screw journaled on said support member;
a guide rail supported by said support member;
a carriage movably connected with said lead screw for linear movement therealong in response to rotation of said lead screw and supported by said guide rail so that said carriage does not rotate with said lead screw, said carriage having said first sensor means connected thereto;
a flexible line having a first end connected directly to said first sensor means and having a second end;
means for connecting said second end of said flexible line to said paddle so that said paddle is rotated when said carriage moves along said lead screw; and
means, responsive to said first speed control means, for rotating said lead screw.

4. An apparatus as defined in claim 3, wherein:
said paddle includes a shaft;
said means for connecting said second end of said flexible line to said paddle includes a sheave coupled to said shaft of said paddle, said sheave having a notch defined therein for receiving said second end of said flexible line and having a circumferential groove defined therein in which a portion of said flexible line is wrapped when said carriage is moved to a first limit position and from which the portion of said flexible line is unwrapped when said carriage is moved to a second limit position;
said first paddle drive means further includes:
first limit switch means, mounted on said support member at said first limit position, for inhibiting the operation of said means for rotating said lead screw when said carriage reaches said first limit position; and
second limit switch means, mounted on said support member at said second limit position, for inhibiting the operation of said means for rotating said lead screw when said carriage reaches said second limit position.

5. An apparatus as defined in claim 3, further comprising a fluid-actuated hoist means, connected to said cabinet, for raising and lowering said paddle relative to said container means.

6. An apparatus as defined in claim 5, wherein:
said pressurizing means further includes:
second pump means, having an inlet for receiving a fluid and having an outlet, for pumping the fluid from said inlet to said outlet;
a rupture disk connected in continuous communication with said chamber;
first conduit means for connecting said outlet of said second pump means to said rupture disk, said first conduit means including first valve means for controllably isolating said outlet of said second pump means from said chamber; and
second conduit means for connecting said first-mentioned pump means to said rupture disk, said second conduit means including second valve means for controllably isolating said first-mentioned pump means from said chamber; and
said apparatus further comprises a pressure gauge mounted on said cabinet and connected in continuous communication with said chamber.

7. An apparatus as defined in claim 1, further comprising a fluid-actuated hoist means, connected to said cabinet, for raising and lowering said paddle relative to said container means.

8. An apparatus as defined in claim 7, wherein said fluid-actuated hoist means includes:
a cylinder attached to said cabinet;
a piston, having a piston rod connected to a piston head, slidably disposed in said cylinder;
means for connecting said piston rod to said paddle; and
fluid means for controllably moving said piston within said cylinder so that said paddle is lifted from said container means.

9. An apparatus as defined in claim 1, wherein:
said pressurizing means further includes:
second pump means, having an inlet for receiving a fluid and having an outlet, for pumping the fluid from said inlet to said outlet;
a rupture disk connected in continuous communication with said chamber;
first conduit means for connecting said outlet of said second pump means to said rupture disk, said first conduit means including first valve means for controllably isolating said outlet of said second pump means from said chamber; and
second conduit means for connecting said first-mentioned pump means to said rupture disk, said second conduit means including second valve means for controllably isolating said first-mentioned pump means from said chamber; and
said apparatus further comprises a pressure gauge mounted on said cabinet and connected in continuous communication with said chamber.

10. An apparatus as defined in claim 9 wherein:
said apparatus further comprises:
master on/off electrical switch means for electrically connecting with a source of electricity;
a drain outlet member mounted on said cabinet; and
third conduit means for connecting said rupture disk with said drain outlet means; and
said pressurizing means further includes:
first fluid inlet circuit means for actuating said second pump means with a driving fluid, including:

first connector means, mounted on said cabinet, for connecting with a source of a first fluid;

a first solenoid valve, responsive to the operation of said master on/off electrical switch means, connected to said first connector means;

fourth conduit means for connecting said solenoid valve with said second pump means, said fourth conduit means including first regulator means for controlling the flow of said first fluid into said second pump means; and fifth conduit means for connecting said second pump means with said drain outlet member; and second fluid inlet circuit means for providing a pressurizing fluid to said inlet of said second pump means, including:

second connector means, mounted on said cabinet, for connecting with a source of a second fluid for use as the pressurizing fluid;

a second solenoid valve, responsive to said master on/off electrical switch means, connected to said second connector means; and sixth conduit means for connecting said second solenoid valve with said inlet of said second pump means.

11. An apparatus as defined in claim 10, further comprising cooling means for cooling said container means with a selectable one of said first fluid and said second fluid, said cooling means including:

a third solenoid valve connected to said first solenoid valve;

a fourth solenoid valve connected to said second solenoid valve;

seventh conduit means for connecting said third and fourth solenoid valves with said container means;

eighth conduit means for connecting said container means with said drain outlet member;

first coolant control switch means, mounted on said cabinet, for actuating said third solenoid valve; and second coolant control switch means, mounted on said cabinet, for actuating said fourth solenoid valve.

12. An apparatus as defined in claim 11, further comprising chamber dump and flush means for dumping and flushing the sample from said chamber, including:

reservoir means, mounted on said cabinet, for receiving the sample from said chamber;

ninth conduit means for connecting said chamber with said reservoir means, said ninth conduit means including third valve means for controllably communicating said chamber with said reservoir means;

a fifth solenoid valve, connected between said first solenoid valve and said third valve means, for switchably communicating said first fluid to said third valve means as a driving fluid for actuating said third valve means;

dump control switch means, mounted on said cabinet, for actuating said fifth solenoid valve;

a sixth solenoid valve, connected between said second solenoid valve and said ninth conduit means, for switchably communicating said second fluid to said ninth conduit means as a flushing fluid; and flush control switch means, mounted on said cabinet, for actuating said sixth solenoid valve.

13. An apparatus as defined in claim 12, further comprising drive cooling means for cooling at least a portion of said first and second paddle drive means, including:

a seventh solenoid valve connected between said second solenoid valve and said portion of said first and second drive means;

tenth conduit means for connecting said portion of said first and second drive means with said drain outlet member; and drive coolant control switch means, mounted on said cabinet, for actuating said seventh solenoid valve.

14. An apparatus for testing the static gel strength of a sample of material, comprising:

a container having a chamber defined therein for receiving the sample of material;

a paddle rotatably disposed in said chamber;

force transferring means for transferring a force to said paddle so that said paddle rotates in response thereto;

a support member;

force sensing means for sensing a force exerted thereon;

movement means for mounting said force sensing means on said support member and for linearly moving said force sensing means; and connector means, connected directly between said force sensing means and said force transferring means, for communicating a force to said force transferring means when said force sensing means moves linearly so that said paddle rotates.

15. An apparatus as defined in claim 14, wherein said movement means includes:

a lead screw rotatably connected with said support member;

a carriage retained on said lead screw for linear movement therealong in response to rotation of said lead screw, said carriage having said force sensing means connected thereto; and drive means for rotating said lead screw.

16. An apparatus as defined in claim 15, wherein:

said connector means includes a line connected to said force sensing means; and said force transferring means includes:

a sheave having a grooved rim and having means for securing said line to said sheave when at least a portion of said line is received in said grooved rim; and coupling means for coupling said sheave and said paddle.

17. An apparatus as defined in claim 16, wherein said force sensing means includes a load cell.

18. An apparatus as defined in claim 17, further comprising:

set point means for setting a value related to a predetermined gel strength for the sample;

comparison means, responsive to said force sensing means and said set point means, for determining when the force communicated through said connector means equals the value related to the predetermined gel strength;

actuation means for actuating said movement means to commence moving said force sensing means; and timer means for indicating the time lapse between when said movement means commences moving said force sensing means and when said comparison means determines the force communicated equals the value related to the predetermined gel strength.

19. An apparatus as defined in claim 14, further comprising:

set point means for setting a value related to a predetermined gel strength for the sample;

comparison means, responsive to said force sensing means and said set point means, for determining when the force communicated through said connector means equals the value related to the predetermined gel strength;

actuation means for actuating said movement means to commence moving said force sensing means; and timer means for indicating the time lapse between when said movement means commences moving said force sensing means and when said comparison means determines the force communicated equals the value related to the predetermined gel strength.

20. An apparatus as defined in claim 19, wherein:

said support member includes:
- a shelf having a first hole defined therein in which said container is retained and having a second hole defined therein; and
- a bracket connected to said shelf below said second hole;

said movement means includes:
- a helically grooved member rotatably supported on said bracket;
- a guide member supported on said bracket;
- a carriage movably mounted on said helically grooved member and retained by said guide member so that said carriage moves along said helically grooved member when said helically grooved member rotates; and
- drive means for rotating said helically grooved member;

said force sensing means includes a load cell connected to said carriage;

said force transferring means includes:
- a sheave; and
- coupling means for coupling said sheave and said paddle; and said connector means includes:
- a line extending through said second hole for connection between said load cell and said sheave;
- a pulley support arm connected to said shelf; and
- a pulley, connected to said pulley support arm, having said line received thereon when said line is connected between said load cell and said sheave.

* * * * *